(12) United States Patent
Jones

(10) Patent No.: US 8,858,607 B1
(45) Date of Patent: Oct. 14, 2014

(54) MULTISPECTRAL THERAPEUTIC LIGHT SOURCE

(71) Applicant: Gary W. Jones, Newcastle, WA (US)

(72) Inventor: Gary W. Jones, Newcastle, WA (US)

(*) Notice: Subject to any disclaimer, the term of this patent is extended or adjusted under 35 U.S.C. 154(b) by 0 days.

(21) Appl. No.: 14/217,356

(22) Filed: Mar. 17, 2014

Related U.S. Application Data

(60) Provisional application No. 61/802,234, filed on Mar. 15, 2013.

(51) Int. Cl.
*A61N 5/06* (2006.01)
*A61N 2/00* (2006.01)

(52) U.S. Cl.
CPC ........... *A61N 5/06* (2013.01); *A61N 2005/0632* (2013.01); *A61N 2005/0652* (2013.01); *A61N 2005/0626* (2013.01); *A61N 2/002* (2013.01)
USPC ................................................ 607/88; 606/9

(58) Field of Classification Search
CPC . A61N 5/06; A61N 2/002; A51N 2005/0632; A51N 2005/0652; A51N 2005/0626
USPC .......................................... 607/88–90; 606/9
See application file for complete search history.

(56) References Cited

U.S. PATENT DOCUMENTS

| | | | |
|---|---|---|---|
| 4,646,743 | A | 3/1987 | Parris |
| 5,800,478 | A | 9/1998 | Chen et al. |
| 5,997,569 | A | 12/1999 | Chen et al. |
| 6,096,066 | A | 8/2000 | Chen et al. |
| D623,308 | S | 9/2010 | Kramer |
| 2004/0127961 | A1 | 7/2004 | Whitehurst |
| 2005/0182460 | A1 | 8/2005 | Kent et al. |

(Continued)

OTHER PUBLICATIONS

Allan, M., "Opportunities in Cancer Therapeutics: Roswell Park Cancer Institute Photodynamic Therapy Patent Portfolio", 2009, pp. 1-4, Publisher: First Principals, Inc., Published in: Cleveland, OH.

(Continued)

*Primary Examiner* — Lynsey Crandall
*Assistant Examiner* — Boniface N Nganga
(74) *Attorney, Agent, or Firm* — Hultquist, PLLC; Steven J. Hultquist

(57) ABSTRACT

A light source apparatus including light spectrum-converting materials that emit light primarily over large portions of the 360 nm-480 nm and the 590-860 nm spectral range is provided. This apparatus provides a cooled, high-luminance, high-efficiency light source that can provide a broader spectrum of light within these spectral ranges than has been cost-practical by using many different dominant peak emission LEDs. Up to 15% of the output radiant power may be in the spectral range 350-480 nm in one embodiment of this device, unless a specific separate source and lamp operating mode is provided for the violet and UV. Control methods for light exposure dose based on monitoring and controlling reflected or backscattered light from the illuminated surface and new heat management methods are also provided. This flexible or rigid light source may be designed into a wide range of sizes or shapes that can be adjusted to fit over or around portions of the bodies of humans or animals being treated, or mounted in such a way as to provide the special spectrum light to other materials or biological processes. This new light source can be designed to provide a cost-effective therapeutic light source for photodynamic therapy, intense pulsed light, for low light level therapy, diagnostics, medical and other biological applications as well as certain non-organic applications.

20 Claims, 4 Drawing Sheets

(56) References Cited

U.S. PATENT DOCUMENTS

| | | |
|---|---|---|
| 2005/0278003 A1 | 12/2005 | Feldman |
| 2006/0030908 A1 | 2/2006 | Powell et al. |
| 2006/0111761 A1 | 5/2006 | Butler et al. |
| 2006/0247741 A1 | 11/2006 | Hsu et al. |
| 2006/0287696 A1 | 12/2006 | Wright et al. |
| 2007/0167999 A1 | 7/2007 | Breden et al. |
| 2008/0119913 A1 | 5/2008 | Powell et al. |
| 2008/0140164 A1 | 6/2008 | Oberreiter et al. |
| 2009/0234340 A1* | 9/2009 | Behrakis ............ 606/9 |
| 2009/0234341 A1* | 9/2009 | Roth ............ 606/9 |
| 2009/0234342 A1* | 9/2009 | Ely et al. ............ 606/9 |
| 2009/0234343 A1* | 9/2009 | Behrakis ............ 606/9 |
| 2010/0087898 A1 | 4/2010 | Clement et al. |
| 2010/0165599 A1* | 7/2010 | Allen ............ 362/84 |
| 2010/0179469 A1* | 7/2010 | Hammond et al. ............ 604/20 |
| 2011/0004201 A1* | 1/2011 | Nuijs et al. ............ 606/9 |
| 2012/0293978 A1* | 11/2012 | Guo et al. ............ 362/84 |
| 2013/0194794 A1* | 8/2013 | Kim ............ 362/231 |
| 2013/0255778 A1* | 10/2013 | Okaniwa et al. ............ 136/259 |
| 2013/0344454 A1* | 12/2013 | Nath ............ 433/29 |

OTHER PUBLICATIONS

Uvbiotek LLC, "Phototherapy systems designed to fit the way you live.", 2006, pp. 1-6, Published in: North Fort Myers, FL.

* cited by examiner

MULTISPECTRAL THERAPEUTIC LIGHT SOURCE

CROSS-REFERENCE TO RELATED APPLICATION

The benefit of U.S. Provisional Patent Application No. 61/802,234 filed Mar. 15, 2014 in the names of Gary W. Jones for "MULTISPECTRAL LIGHT SOURCE" is hereby claimed under the provisions of 35 USC 119. The disclosure of U.S. Provisional Patent Application No. 61/801,602 is hereby incorporated herein by reference in its entirety, for all purposes.

FIELD

The present disclosure relates to a multispectral light source having utility for light therapy and other applications.

DESCRIPTION OF THE RELATED ART

Light therapy devices and methodologies that have been publicly reported or claimed include (1) Low level light therapy (LLLT) for the treatment of inflammation and/or for tissue surface, other tissue healing, skin and tissue rejuvenation, muscle growth enhancement, muscle repair and pain reduction, accelerated tendon healing, joint or cartilage treatments, plantar fasciitis, pain management, traumatic brain injury (TBI) damage risk reduction, neurologic rejuvenation, enhancing stem cell generation, enhancing mood, and/or enhanced rate healing of wounds, blood and body fluid treatments (with or without photosensitizers), spider vein and/or varicose vein and/or scar and/or stretch mark reduction treatments with or without photosensitizers, reducing arterial plaques or other undesired biological materials using photosensitizers, treating biofilms on natural and/or man-made surfaces in or on the body, carpal tunnel, fibromyalgia, tendonitis, bursitis, tendonitis, migraines, carpel tunnel, osteoarthritis, dental root and implant healing or bone regrowth, for enhancing the rate for other bone healing, accelerating T-cell life cycles and activity, accelerating macrophage action, veterinary applications, and/or providing many other health related medical benefits, (2) Activation of photosensitizers used in Photodynamic therapy (PDT) for cancer or antimicrobial treatments using natural or synthetic photosensitizers, including photosensitizers produced by bacteria in or on the body, (3) Imaging and diagnostics using the emitted light spectral range, (4) Intense Pulsed Light (IPL) therapies, sidereal or other mood therapies, (5) activation of adhesives or scaffolding agents as a part of reconstructive or cosmetic surgery, (6) photoactivation of release agents to separate structures of compounds for surfaces, (7) powering of photocell driven devices in the body, and/or (8) other uses such as light-sensitive chemical activation, and/or use of this light therapy in combination with ultrasonic, vibration, thermal heating or cooling, and other combinational therapies.

Non-therapy biological uses of devices using parts of these spectral ranges are (1) Enhancing plant growth, blooming, and/or ripening, (2) Enhancing algae growth, photo-bacteria growth, and other photosynthesis or other photosensitive biological processes, (3) microbial stimulation, (4) increasing antimicrobial action on or in materials using photosensitizers (e.g., water or foods), and/or (5) visual image enhancement for enhanced detection of materials with unique light absorption and emission characteristics.

The accessibility and effectiveness of these therapies can be enhanced by a collective matrix of improved energy efficiency, higher light intensity, generating light more efficiently, transmitting light into tissue more efficiently, reduced unintentional heating of the illuminated tissues, covering larger portions of the therapeutic spectral ranges than practical with conventional LEDs and lasers, enabling easy-to-produce flexible designs, ease of integration with many other therapies, and/or lowering the complexity and potential cost of multi-wavelength light therapy systems.

For deep-tissue and deep nerve, brain, joint, or bone therapy applications, this multifaceted need for lower cost, high intensity, efficient to transmitting light into tissue, comfortable light sources is very important. Above 650 nm light is considered most useful for penetrating deeper into tissue, although the energy per photon available to induce photochemical processes decreases as the wavelength increases, rather than just radiant heating. Since multiple light spectrum and intensity influenced biological processes exist, and light penetration varies by tissue type and wavelength, a broad spectrum light source covering most of the Orange to Near-Infrared (ONIR) spectral range light range within 595-860 nm, is important.

Conventional light therapy methods covering wavelengths within the ONIR spectral ranges compromise important parameters excessively to the point where few are effective using practical exposure times, or are very expensive. Also, LED and laser light sources are typically restricted to a few wavelength peaks with less than a +/−30 nm spread to under 10% of the peak light emission for each type of LED unless many LEDs or lasers are combined.

Light sources used for activating photosensitizers typically use narrow spectrum light from lasers or non-laser LEDs, although other light sources such as filtered halogen light sources or even sunlight and room ambient are sometimes used for dermatology PDT. Multiple photosensitizers and reporters may be used together, and may require multiple excitation wavelength ranges or broad spectrum activation light. LLLT processes and photosensitizer activation processes may be used in combination processes.

Light spectrum and intensity output with some similarity to those provided by the invention described herein can be obtained by other types of light sources: (1) using mixtures of multiple different color LEDs and/or laser diodes, but this can be expensive and more complicated to manufacture at low cost for large area light sources, and (2) by filtering out light at some wavelengths of light from broad-spectrum light sources such as gas discharge lamps, fluorescent, or halogen lamps but these techniques are also expensive, generate excessive heat, and waste energy when applied to large area high intensity lighting applications.

Fluorescent dyes, quantum dots, and phosphors have been used for printed fluorescent signs and paints; dye or phosphor conversion of blue LEDs into white LEDs have been used for visible lighting, display backlights, in instrument panels, and converting sunlight more into longer wavelength spectral ranges to improve solar cell efficiency, and many other applications.

Light sources using spectrum conversion with photoluminescent dyes, phosphors, pigments, quantum dots or other nanoparticles, photonic crystals and other materials or nanostructures are known and many spectrum conversion methods are widely used in many commercial lighting products such as white LEDs, displays, fluorescent light bulbs, and many other applications. The use of red phosphors is known with 660 nm and 670 nm phosphors being commercially available. The use of multiple tandem phosphors is known (US 2012/0043552 AI) to down convert to longer wavelengths, although light losses occur at each conversion. Dyes with light emission characteristics in the red to near IR range are also known.

Currently available light spectrum spectral conversion or shifting technologies provide relatively low overall light spectrum conversion efficiency and/or costly conversion of 360 nm-650 nm spectral range input light into the ONIR spectral range above 650 nm. Many current light therapy sources also only provide light in small portions of the ONIR spectral range, generate excessive amounts of heat, require high input power and poor energy efficiency, provide low efficiency light transmission into the tissue, are not sufficiently photostable, and costly in systems that can provide deep penetrating near-IR light at high intensities (even over 50 mW/cm2).

Up to 80-85% internal quantum yield (QY) red phosphors are available at high cost per gram, while lower-cost red phosphors may be under 60% internal quantum yield and less stable. Small amounts of lower cost red phosphors are now commonly combined with YAG:Ce cool-white phosphors (mixed or in subsequent parts of the light source) to make warm-white LEDs. Light scattering by phosphor particles and phosphor matrix adsorption losses can cut the output light efficiency by another 20 to 30%, depending on the amount of phosphor used and overall design used due to internal scattering by phosphor particles and other losses. Higher concentrations of phosphor particles or a larger volume phosphor matrix is needed for over 80% light conversion to the phosphor's spectral emission range, but this can reduce the external QY efficiency by another 30%. Near IR phosphors have been shown, but few good choices are available commercially at this time.

Quantum dots (QDs) are available commercially in many different spectral ranges for lighting, displays, and for biological labeling and staining. QDs are just beginning to become available commercially at pricing potentially suitable for light sources. QDs can provide good QY in the 70-90% range, exhibit lower scattering losses than phosphors, and can function in a wider range of polymer medium than most high performance photoluminescent dyes.

Organic dyes in polymer matrices that exhibit high quantum yield in the over 90% range for ONIR light have generally not been seriously considered sufficiently stable for high luminance light sources, have only recently become commercially available, and/or have poor extinction coefficients in the desired light absorption spectral ranges so they require large quantities of dye when >90% of the incoming light is to be converted into the ONIR spectral range. Conversion of violet or blue light to ONIR light using most organic dyes requires a large stokes shift or multiple stacked dyes, resulting in poor photostability, added complexity, high cost, and poor energy efficiency. Fluorescent dyes are typically not used in LEDs as it has been non-obvious how to accomplish this using available dyes in reasonable medium, photostability issues, and the stokes shift is usually small so most red emitters tend to absorb poorly in the violet-blue.

Non-fluorescent dyes are sometimes used as filters to absorb portions of the light spectrum to provide more pure visual color, but absorption filtering wastes a significant amount of light and is usually undesirable for our applications unless it is to block UV or long wavelength IR.

Biological applications for fluorescent dyes, quantum dots, and phosphor-like nanoparticles have included tagging and tracking of biological materials, and use as photosensitizers or in photodiagnostic systems. Photoacoustic applications have also been reported. Most ONIR range photoluminescent materials are very expensive per gram of dye, not very high quantum yield, and/or provide poor stability in use. Fortunately, many medical dye applications do not require as high photostability as solar cell conversion or other lighting applications, high quantum yield and high extinction in the red to near-infrared spectral range. Unfortunately, minimal heat producing, high intensity light source applications for light therapy, as an example, do require all the parameters to be simultaneously met.

Even though the name "low level light therapy" or LLLT implies the use of low-intensity light, high-intensity light (>10 mW/cm2 or even >100 mW/cm2) is frequently desired to reduce the treatment time, or to obtain adequate intensities of Red and near-infrared (NIR) light into deep-tissue where the light intensity may be several orders of magnitude lower than at the tissue's surface. Even deep penetrating NIR light intensity may be 1,000-10,000× lower at 4-8 centimeters below the skin surface than at the light source. Considerable light is lost in many systems just due to unrecovered skin reflection losses. Almost no practical products available to consumers or clinics provide the total absorbed light dose necessary for treatment over 4 cm deep in tissue and/or through living bone in an under 30 minute exposure time per location, and those that do provide high intensity light are typically expensive and require high power lamps and/or extensive heat control capabilities.

Many light therapy systems have been shown.

Non-photosensitizer PDT and LLLT may use narrow spectrum light, multiple peak spectrum light, or broad spectrum light to penetrate different depths through different types of tissue and/or to activate or drive different chemical and biochemical processes or different photosensitizers. While certain narrow spectrum wavelengths may be optimal for certain processes, a range of wavelengths can be more desirable for LLLT, some single photosensitizer PDT making use of different penetration depth of different wavelengths of light, multiple photosensitizer PDT, PDT with separate diagnostics, multiple fluorescent reporter applications, and some combined PDT and LLLT treatments.

Intense pulsed light (IPL) is used for many treatments with lasers, gas discharge, or halogen lamps. Non-laser LEDs can also deliver high intensity pulsed light, especially if focused or otherwise condensed (e.g., using tapered fiber optics). These treatments are frequently used for hair reduction and for treating a variety of skin conditions such as acne, wrinkles, dark skin discolorations, moles, or rosacea.

Small area LED and laser light sources (direct illumination or through fiber optics) can be used for applications where the light is directed at a specific tissue-surface target, such as a basal cell carcinoma. However, for deep tissue light treatments without the use of skin-penetrating probes, the light scattering effects for small area sources reduce the effective light intensity at large depths through tissue significantly. Light sources with large illumination areas relative to targeted tissue deep under the skin reduce the effective transverse losses due to lateral light scattering by tissue, cartilage, or bone behind the center zone of the light source and therefore can provide higher light intensities much deeper in tissue and bone than is practical with small area light sources. Conformal light sources can further improve light coupling efficiency.

Of the light that is actually incident on the tissue surface, up to 50% or more of the incident light is reflected off of and/or backscattered out of the tissue and is lost for therapeutic purposes in most commercial system designs. (This includes laser and non-laser LEDs, other lasers, IPL, OLED, and other light sources).

Therapeutic light sources with high reflectance to return reflected or backscattered light to the tissue can provide superior therapeutic and diagnostic depth through tissue effectiveness range.

Direct skin surface exposure during LLLT frequently can require long exposures per location even if very high light intensities are supplied, depending on the incident light intensity, spectral range of the light, light source and tissue characteristics, depth of light penetration desired, and the light dose at the targeted tissue required. This is due to high scattering and absorption losses even for the best penetrating near-IR light, even with large area light sources that effectively reduce some of the scattering losses. This can be very difficult to practically accomplish using typical under 10 Watt lamp power consumer handheld or small mounted systems unless strapped to the body for long periods of time. Without the light source shaped to the body, reflection and backscatter light loses cannot be minimized. Therefore, easily adjusted, comfortable, and/or body shaped body-mounted light source systems are usually more practical than handheld units or non-conformal light panels.

In addition to the efficient generation of the selected therapeutic and/or diagnostic light spectra by the LEDs or other light generating devices, if the light generated is incident on the surface tissue over a large area with the illuminated area being large relative to the targeted tissue (especially if light can be directed in from multiple sides of the target like a strap all, or part way around a body part), higher effectiveness can be provided. Furthermore, much of the reflected or backscattered light from the tissue surface should be reflected back at the tissue surface. Occasional movement of the light source can be used to further enhance the amount of light delivered deeply over a larger area. This is all known, although seldom well-practiced.

At the desired high light intensities and treatment duration times desired for deep-though-tissue or into-bone treatments, heating of the tissue surface can becomes a major issue for conformal light sources. Heating of tissue surfaces in conformal systems held against the tissue surface and cost of high efficiency light emitting devices at the desired wavelengths has forced compromises that result in many LLLT products on the market to be largely ineffective and caused most PDT products to be higher cost than desirable. Compromises in current products have included: (1) too low effective light intensity, (2) non-optimal light spectra or incomplete complement of wavelengths, (3) inability to achieve deep-in-tissue light doses in practical time periods, (4) poor therapeutic light transmission deep into tissue, and (5) overheating of tissue surface discomfort.

Conformal light sources in near-direct contact with the target tissue and that reflect reflected light back to the tissue to be illuminated can best efficiently direct light into tissue, although available systems do this poorly.

To optimize the total light absorbed by tissue to tissue surface heating in an efficient manner, 3 integrated innovations are necessary for many non-photosensitized based light therapies, and some diagnostics or photosensitizer based applications.

Efficient and economical generation of light covering a large percentage of the spectral range of wavelengths potentially useful for activation most LLLT biological processes (595-860 nm), and other specific wavelength ranges such as 390-440 nm (antibacterial, but above the UVA spectral range).

An improved method for reflection of light back into the tissue surface while still reducing heat transfer to tissue in a conformal-to-tissue-surface light source.

Simultaneous control of radiant heat, conduction of heat, and convection heating of the tissue surface when high intensity large area light sources are used, coupled with cooling methods on the skin.

A design that can utilize these multiple methods together can enable higher intensity light sources to be used or longer treatment times per location with less discomfort from skin heating during PDT or LLLT.

System controls: Timers, over-temperature limiting devices such as thermocouples with control circuits, mechanical or electronics temperature limit switches, IR thermal measurement of skin or device surfaces, and/or the use of controller electronics to increase cooling or reduce energy to the system are all known methods for keeping the devices from overheating skin, the light source(s), or other surfaces. These controls may not always be necessary for light sources with adequate cooling capability, reasonably high energy efficiency, and sufficiently low power if the devices are used properly in open air below 30 deg. C.

Controllers with data logging and/or RF call of attendant upon overheat, timer completion, improper operating conditions, and/or patient activated attendant call-notification capability are all anticipated.

People with different skin or tissue absorption, different skin coatings, different hair type or density, different types of tissue and biological materials, or different non-biological materials may experience different amounts of heating, light absorbance, presence of photosensitizers or reporters, and/or reflectance. This may occur especially when using a broader spectral range light source for therapy, diagnostics, or non-biological chemical activation.

An IR heat sensor and one or more ONIR light sensors may be used to determine the amount of light being absorbed by the tissue and the surface heating, allowing for partial or total near-optimization of the total light dose and light intensity to correct for different skin types and tissue types being treated.

Thus, an over 10 mW/cm2 broad spectral emission ONIR light therapy system that emits light conformably over a large area economically and provides adequate controls for all or most of the parameters discussed in this section, may provide significant benefits for a wide variety of biological and medical applications. The optional addition of up to 50% violet light to ONIR light can provide antibacterial benefits for skin that can be further enhanced using photosensitizers.

SUMMARY

The present disclosure relates to a multispectral light source having utility for light therapy and other applications.

More specifically, the disclosure relates to a light emitting device combined with a spectrum converter and power supply to provide a primarily non-coherent output light source that efficiently generates and provides a customizable spectral range light. Optional features, such as heat sinks, can be applied to specific embodiments. The output photon flux provided by this light source is mostly within the orange-to-near-infrared (ONIR) 595 nm-860 nm spectral range, and with light energy at all wavelengths within this ONIR spectral range. 350 nm-to-465 nm and 595 nm-to-960 nm light may also be present in some light therapy system embodiments.

This new light source apparatus uses multiple new light spectrum converting materials and device structures that can absorb light in one spectral range from light emitting devices such as LEDs or laser diodes, and then reemit most of the absorbed photons in all or part of the ONIR spectral range.

This light source device can provide a much higher quantum-efficiency and cost-effective way to provide broad-spectrum ONIR light output than current commercially available technologies with reduced surface heating for use in several applications, including photodynamic therapy (PDT), low level light therapy (LLLT), light influenced biological processes, diagnostics, lighting for photo-luminescent based imaging, and/or other medical and non-medical applications.

An objective of the present invention is to efficiently provide output photon flux over all or almost all of the ONIR spectral range in order to provide reasonably efficient transmission of the ONIR light into the surfaces being illuminated. Objectives for this device include accomplishing the generation of broad spectrum ONIR light at lower system cost, higher energy efficiency, ability to exceed 10 mW/cm$^2$ light intensity to the surface to be radiated, to be scalable for large areas of light exposure exceeding 100 cm$^2$, and/or with the potential for less heating of the illuminated surfaces than most other conventional light source devices.

While light spectrum conversion is known and used in many applications, this device more efficiently performs the spectrum conversion to produce light over most of the ONIR range with unique spectral results, provides a unique spectrum conversion structure using new materials in a novel way, and also provides additional light exposure control options and/or heat management structures. These device embodiments and methods are uniquely suitable to medical and other biological applications, but also suitable for non-organic applications. The invention provides examples of several embodiments of the invention, as well as related components, systems, and methodology.

In one aspect, the disclosure relates to a light emitting device for generating a predominantly non-coherent output light, comprising one or more spectrum converters, one or more LEDs, and one or more power supplies arranged for energizing the one or more LEDs, wherein the device is configured to produce the output light with an output photon flux that is predominantly in the orange-to-near-infrared (ONIR) 595 nm-860 nm spectral range, and with light energy at all wavelengths within such ONIR spectral range, wherein the light emitting device is characterized by the following characteristics: (a) one or more of the LEDs are overlaid with one or more spectrum-converting fluorescent and/or phosphorescent containing materials or photonic spectrum-shifting structures, as said spectrum converters; (b) spectrum converting LED light sources in the light emitting device are configured to contribute over 25% of the total output radiant light power of the output light; (c) quantum yield of spectrum converters averages over 60% when independent of the light emitting device and under optimal conditions; (d) one(s) of the one or more LEDs to be spectrum converted provide dominant spectral emission peaks between 350 nm and 480 nm and/or between 600 and 780 nm; (e) 350 nm and 480 nm dominant peak LEDs with spectrum converters use a phosphor or QD as the spectrum converter for absorption of over 70% of the LED radiant power light; (f) 600 nm-780 nm dominant emission peak LEDs with spectrum converters use a fluorescent dye or QD spectrum converter for absorption of over 30% of the LED radiant power light; (g) over 70% of the total output light from the device is in the 595-960 nm spectral range; (h) at least 1% of the highest radiant power peak in the 600 nm-750 nm part of the emitted light spectrum of the output light is provided at all wavelengths between 600 nm and 820 nm; (i) LED(s) of the one or more LEDs, whose light is not significantly absorbed by the spectrum converters comprise LEDs with dominant peak wavelengths within the 350 nm-480 nm spectral range and/or within the 650 nm to 860 nm spectral range; (j) the device comprises a lighted window at which the light output is emitted, and the device emits at least 0.01 mW/cm$^2$ average radiant power output in a primary lighted portion of the lighted window and the primary lighted portion of the lighted window comprises a lighted area of at least 4 cm$^2$; (k) at least 20% of the primary lighted portion of the lighted window contains over 30% light reflective surfaces at the highest spectral emission peak of the output light, to reflect light back into the output light; (l) LED light is provided by at least one of the one or more LEDs behind the lighted window, in the perimeter of the lighted window, or brought to the lighted window using fiber optics; (m) a thermal controller is arranged to interrupt or reduce power from the one or more power supplies when temperature of or in the device exceeds a predetermined value; and (n) wherein when the LED light is not brought to the window by fiber optics, the thermal controller is effective to prevent temperature of the device from exceeding 60° C. after 60) minutes of device operation in a 35° C. ambient environment.

In another aspect, the disclosure contemplates an LED array light source comprising channels arranged for peristaltic air pumping when the light source is bent and/or moved to increase convection flow in and out of the channels to effect heat removal from the LED array.

The disclosure also contemplates a method of light therapy treatment of a subject in need thereof, said method comprising generating a modified light spectrum output using a device according to the present disclosure, and exposing a body region of the subject to the light output thereof.

Other aspects, features and embodiments of the disclosure will be more fully apparent from the ensuing description and appended claims.

DETAILED DESCRIPTION

Figure 1:
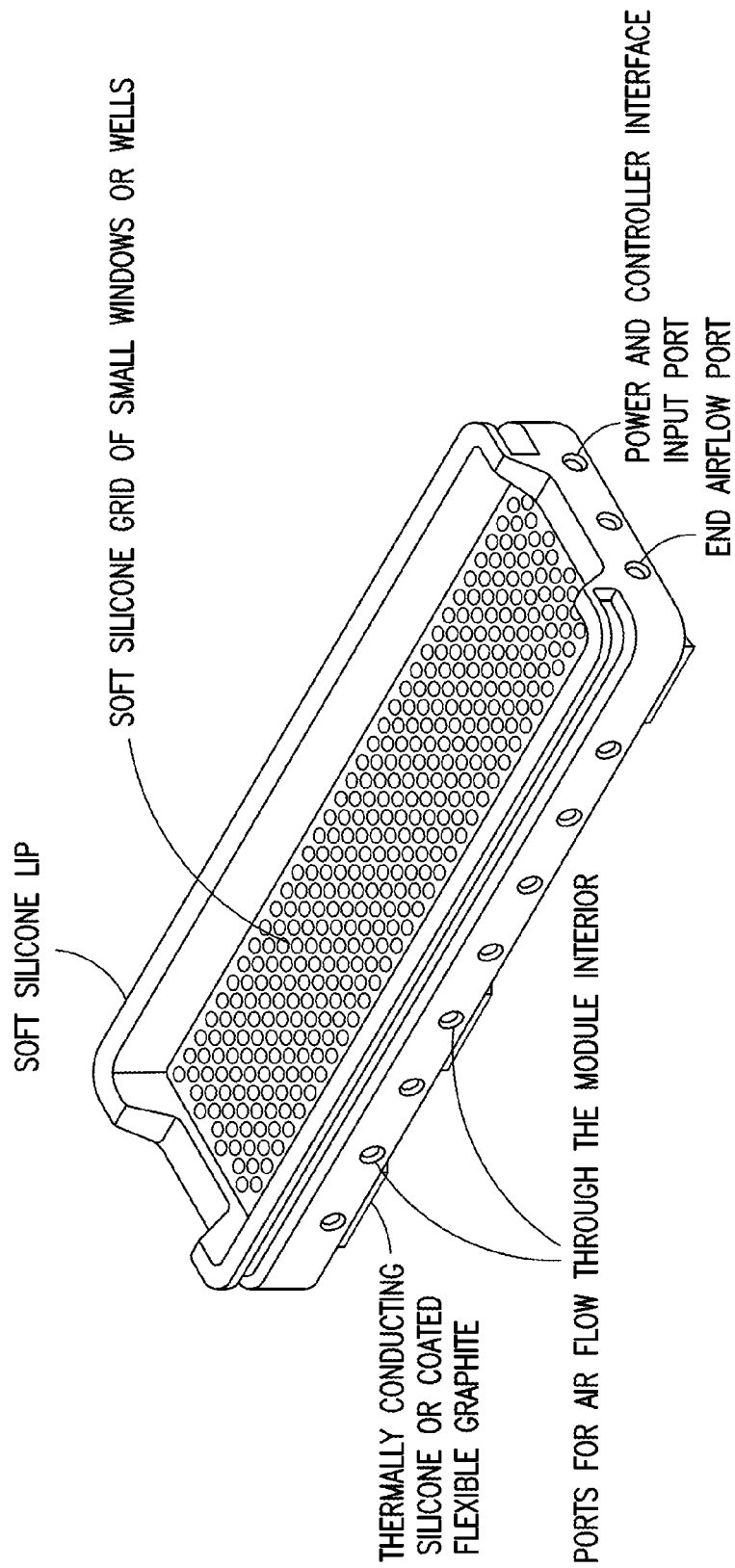
FIG. 1 is a top perspective view of a light therapy module according to one embodiment of the present disclosure.

The present disclosure relates to a multispectral light source having utility for light therapy and other applications.

LEDs, as such term is used herein, should be understood to mean both non-coherent diodes and laser diodes. LEDs and laser diodes are collectively referred to as LEDs herein. Although the disclosure is directed to multispectral light source devices including spectrum-converted LED arrangements, it will be understood that non-converted LEDs may be employed in such devices, within the broad scope of the present disclosure.

Although certain embodiments of the invention will be shown and described in detail, it should be understood that various additional changes and modifications not specifically described herein may be made without departing from the scope of the invention described herein. The scope will in no way be limited to the number of constituting components, the materials thereof, the shapes thereof, the relative arrangement thereof, etc., and are disclosed simply as examples of embodiments.

As used herein, the following technical terms have the following meanings:

"nm" means Nanometers ($10^{-9}$ meters length).

"OCST" means other color shifting technologies, including photonic crystals, QDs, photonic spectrum converting fibers, photoluminescent fibers, and/or crystal arrays or matrices including combinations of these and other color converting technologies.

"PDT" means Photodynamic therapy or the use of light as part of a therapy of diagnostic. In this document we will only refer to PDT as light therapy using photosensitizers.

"Photoluminescent" means any characteristic where light of one spectral range is first absorbed by a material, and then all or part of this absorbed energy is later emitted to provide a different spectrum of wavelengths. This term includes both fluorescence and phosphorescence.

"PS" means photosensitizer, a compound or particle that absorbs light and initiates or engages in chemical reactions using the light energy.

"Reporter" means photoluminescent compounds or particles that absorb one spectrum of light and emit another spectrum of light, generally used to assess the presence and/or concentration of a photoluminescent material and 'report' this information to optical sensors (or acoustic sensors if photo-acoustic reporters are used).

Quantum yield means the ratio of emitted photons/absorbed photons from a material for a specific excitation spectrum. It is shown as percentage without units.

"∈" means extinction coefficient in M−1 cm-1. "Extinction" shown as the symbol epsilon (∈) refers to the probability of a dye or other material absorbing photons at a specific wavelength. A higher number means a high probability of absorbing photons at a wavelength. If a reference wavelength is not explicitly referenced, it is assumed that the extinction coefficient refers to the maximum major extinction or absorption peak that is shorter wavelength then the maximum emission peak for the photoluminescent material. "Extinction" does not directly apply to some materials even though all the photoluminescent materials exhibit similar photo-optical characteristics, so "effective extinction" may be referred to in some relative context references.

"ONIR" means Orange to Near-Infrared spectral range light (595-860 nm) While many people consider near infrared light to extend past 900 nm, we have confined the ONIR range for the specific applications herein to be 595-860 nm.

"IR" means Infrared: Light in the spectral range above 860 nm.

"NIR" means Near-infrared: Light in the 720-860 nm range (slightly visible to most people even at moderate intensities).

"Red" means 620-720 nm light.

"Orange" means 595-620 nm light.

"RNIR" means red to near-infrared spectral range light (620-860 nm).

"UV" means ultraviolet light with wavelengths in the 100-400 nm range.

"UVA" means ultraviolet light with wavelengths in the 315-400 nm range.

"UVB" means ultraviolet light with wavelengths in the 280-315 nm range.

"VIO" means Violet to orange spectral range light (385-620 nm).

"VIB" means violet to blue spectral range light (385-490 nm).

"VIY" means violet to yellow spectral range light (385-650 nm).

"Violet spectral range" means 385-435 nm.

The present disclosure contemplates a light emitting device combined with a spectrum converter and power supply to provide a primarily non-coherent output light source that efficiently generates and provides customizable spectral range light.

In one aspect, the disclosure relates to a light emitting device for generating a predominantly non-coherent output light, comprising one or more spectrum converters, one or more LEDs, and one or more power supplies arranged for energizing the one or more LEDs, wherein the device is configured to produce the output light with an output photon flux that is predominantly in the orange-to-near-infrared (ONIR) 595 nm-960 nm spectral range, and with light energy at all wavelengths within such ONIR spectral range, wherein the light emitting device is characterized by the following characteristics: (a) one or more of the LEDs are overlaid with one or more spectrum-converting fluorescent and/or phosphorescent containing materials or photonic spectrum-shifting structures, as said spectrum converters; (b) spectrum converting LED light sources in the light emitting device are configured to contribute over 25% of the total output radiant light power of the output light; (c) quantum yield of spectrum converters averages over 60% when independent of the light emitting device and under optimal conditions; (d) one(s) of the one or more LEDs to be spectrum converted provide dominant spectral emission peaks between 350 nm and 480 nm and/or between 600 and 780 nm; (e) 350 nm and 480 nm dominant peak LEDs with spectrum converters use a phosphor or QD as the spectrum converter for absorption of over 70% of the LED radiant power light; (f) 600 nm-780 nm dominant emission peak LEDs with spectrum converters use a fluorescent dye or QD spectrum converter for absorption of over 30% of the LED radiant power light; (g) over 70% of the total output light from the device is in the 595-960 nm spectral range; (h) at least 1% of the highest radiant power peak in the 600 nm-750 nm part of the emitted light spectrum of the output light is provided at all wavelengths between 600 nm and 820 nm; (i) LED(s) of the one or more LEDs, whose light is not significantly absorbed by the spectrum converters comprise LEDs with dominant peak wavelengths within the 350 nm-480 nm spectral range and/or within the 650 nm to 860 nm spectral range; (j) the device comprises a lighted window at which the light output is emitted, and the device emits at least 5 mW/cm$^2$ average radiant power output in a primary lighted portion of the lighted window and the primary lighted portion of the lighted window comprises a lighted area of at least 4 cm$^2$; (k) at least 60% of the area of the primary lighted portion of the lighted window contains over 30% reflective surfaces at the highest spectral emission peak of the output light, not including area used by LEDs or spectrum converters, to reflect light back into the output light; (l) LED light is provided by at least one of the one or more LEDs behind the lighted window, in the perimeter of the lighted window, or brought to the lighted window using fiber optics; (m) a thermal controller is arranged to interrupt or reduce power from the one or more power supplies when temperature of the LED heat sink or the LEDs in the device exceeds a predetermined value; and (n) wherein when the LED light is not brought to the window by fiber optics, the thermal controller is effective to prevent the skin or tissue facing side surface temperature of the device from exceeding 70° C. after 60 minutes of device operation in a 35° C. ambient environment. Lower temperature values can be selected.

Optional features such as heat sinks can be applied to specific embodiments, as well as other optical elements such as diffusers, gratings, lenses, filters, and light sensors.

In the device of the disclosure, the spectrum converters may comprise a phosphor, fluorescent or phosphorescent dye, and/or quantum dots with substantial light absorption in the under 480 nm spectral range, and/or a fluorescent dye or photonic crystal structure with the majority of its absorption spectrum in the under 650 nm spectral range, and where over 70% of light emission from the spectral converters is within the 595 nm to 960 nm spectral range.

The device may be configured as comprising rows or columns of said LEDs on one or more flexible circuit connection backing arrangements, and/or comprising a multiplicity of rigid LED modules that can be placed so as to provide therapy light from two or more angles. LEDs may be arranged linearly as one or more rows on flexible circuit strips with reasonable backside heat removal capability. These types of flexible circuit strip modules are common in the market for standard LEDs, but require custom LEDs and also require PCBs with backside heat removal if true therapeutic light radiance is desired for less than 1 hour exposures of joints in body parts larger than fingers. LEDs may be arranged as small rigid linear or 2D circuit board, metal, or ceramic blocks and connected to that function like a tank tread. These types of circuit modules are common in the market for standard LEDs, but require custom LED processing. LEDs may the arranged in medium or large rigid arrays. These arrays may be organized like tanning beds or put on racks to expose the body from one or more sides. Many design arrangements exist or are possible.

The device may be configured, as comprising control circuitry configured to operate the device at a constant luminance, or modulated at one or more frequencies and at one or more duty cycles. Modulation frequencies between 6 Hertz and 20K Hertz may be used for direct light therapies. Modulation frequencies between 20K Hertz and 110M Hertz may be used for driving photoacoustic imaging or therapeutic processes.

In various embodiments, the device may comprise a backside heat sink structure comprising heat conducting belt loops configured to dissipate at least 25% of the total heat load from the one or more LEDs and/or comprising sections of heat conducting belts in contact with said belt loops, e.g. heat conducting belt loops that can dissipate at least 25% of the total heat load from the LEDs. This heat sink structure may be flexible or rigid. Any of many effective and well known heat transfer coupling methods the LEDs to the backside heat radiator may be used such as thermal conducting silicone adhesives or silicone tape and other thermal conductors known to fill or conform to gaps between surfaces such as thermal conducting grease. Materials of construction can be almost any environmentally stable, safe to use, structurally adequate as a belt or belt loop heat conducting material exhibiting over 0.1 W/m·K thermal conductivity such as many metals, composite materials such as polymer encapsulated graphite or carbon fibers, or polymers with heat conducting additives.

The device may comprise a backside heat sink structure, e.g., a structure that permits air flow around and/or through a backside radiator that includes four or more heat conducting materials formed as fins, waves, tubes, or folds bonded to a heat conducting base structure. The baseplate of the heat sink structure may be mostly flat, or have its own structure such as secondary waves, ridges, fins, grid including a wire or strip grid, and/or embossing of any design. The folds or waves may be square, triangular, trapezoidal, cylindrical, rectangular or semi-rectangular tubes, curved, wave-like, have flat top or bottoms, or almost any other shape that provides an air path under or under and/or through the heat sink structure and a reasonable thermal connection to the base plate or through an alternate overall underlying thermal path to the LEDs (such as a thermal conducting thermal adhesive or grease protruding through a mesh baseplate to the heat radiators). The folds or waves may be repeating or be a mixture of shapes. Multiple layers of the folded wave structure may be superimposed or interdigitated. The folded heat sink appearance may be derived from actually folding the material or by forming or molding the material into a similar structure.

For all of these backside or perimeter of the thermal module heat sinks, the heat sink structures may be optionally painted, embossed, brushed, anodized, and/or polymer coated. These heat sink structures must be thermally connected each other or to the LED modules in a way to allow sufficient heat transfer to occur. Braising, gluing, clamping, stapling, clamping with thermal grease or other thermally conductive bonding are acceptable if appropriate materials are selected. These heat sink structures may be made from almost any reasonably thermally conductive, environmentally stable and safe to handle metal such as aluminum or an aluminum alloy, plated copper, and/or laminated metal such as aluminum laminated over copper. Metal can be cast metal (sectioned blocks, linked together in some way or thin enough between sections to bend, sheet metal (single or multiple), folded sheet metal, perforated metal sheet metal, or wires bound together in a screen of any arrangements or be placed in a parallel orientation, and/or any combinations of these and other heat conductor arrangement. These heat sink structures may be a non-metal such as polymer encased graphite, thermally conductive silicone with carbon fibers, metal filling, alumina or diamond particle filling, and/or other thermal conducting materials. Combinations of heat sink materials are permitted as long as the base material conduction heat from a thermally conducting interface between the LEDs and the base material to the heat conducting waves or an underlying heat conducting material transfers heat efficiently to the heat radiating folds or wave structure. Fans, thermoelectric coolers, pumped liquid through a recirculation system and through heat exchangers, or forced air cooling through tubes and through the device (with or without refrigeration of the air), and other well-known cooling methods may be optionally used to further enhance heat removal in situations where the ability to remove heat locally is restricted or undesirable. Multiple rigid modules may be linked together to form pods that can be organized into linear or 2D arrays than can then be shaped into 3D arrays such as whole or partial cylinders to go around body parts or people.

The device may be constructed, wherein the lighted window comprises one or more windows on a top side of the device where the light output is emitted, wherein: the active-light window area in front of the LEDs has one or more translucent windows providing low thermal conduction to the skin or other tissue, comprising a 2D or 3D matrix of liquid, gel, or air filled gas pockets or channels, and comprising low-thermal conducting top surface materials; air or gas is flowed through the pockets or channels to improve heat removal; bumps and/or raised patterns and/or recessed patterns are disposed between two or more transparent layers between the one or more LEDs and the windows; bumps or fiber-like extensions of surface material, or a matrix of LED-coupled fibers protrudes through a window; a top outer surface of a window comprises a grid of wells to provide air pockets to reduce heat transfer through the windows and/or to hold materials for application to the skin; and/or the lighted window is formed of a low index of refraction silicone or multiple layers of low index of refraction coatings or films are provided at a surface of the lighted window.

The light source device may thus be provided with one or more windows on the topside of the device where light is emitted where: the active-light window area in front of the LEDs has one or more translucent windows providing low thermal conduction to the skin or other tissue, consisting of a 2D or 3D matrix of liquid, gel, or air filled gas pockets or channels, and the use of low-thermal conducting top surface materials such as translucent soft silicone; air or gas may optionally flow through these pockets channels to improve heat removal: bumps and/or raised patterns and/or recessed patterns such as rows, columns, and/or grids (horizontal and vertical grid heights can be the same or different) between 2 or more transparent layers between the LEDs and the surface of the window may also or alternatively be used to reduce heat transfer from the LEDs to the front surface; bumps or fiber like extensions of the surface material, or a matrix of LED coupled fibers protruding through the top window to direct light through hair to skin as an option: the top outer surface of the window that would rest against the skin may have a grid of small wells approximately 0.5-20 mm in length or width and 0.1-10 mm deep to provide an additional layer of air pockets to reduce heat transfer through the transparent window and/or to hold emoluments, gels, liquids, index mating materials, drugs including photosensitizers, or other materials against the skin; and/or the top window may be made of low index of refraction silicone or use multiple layers of low index of refraction coatings or films at the interface of the skin and the window to improve light transmission into the skin. This includes the use of removable films such as oils or waxes and other coatings on the window or skin to provide a stepped index of refraction and closer coupling index of refraction with that of the skin ($\eta=1.35$-$1.42$ range).

In another aspect, the disclosure contemplates an LED array light source comprising channels arranged for peristaltic air pumping when the light source is bent and/or moved to increase convection flow in and out of the channels to effect heat removal from the LED array. This may be used to assist front side and/or backside heat removal. The light source may be fabricated so that underneath the window-like surface structure and part of the same molded part is an array of transparent vertical polymer (e.g., silicone) walls that are laid out in a matrix so that the underside vertical walls of the silicone meet with and partly seal over the LED strips that are recessed into the bottom thermally conducting silicone. This array acts like an airgap insulator between the heat producing LED arrays the patient. However, even with good heat sinking out the backside, the air in these pockets can become heated.

The sides of wells in one direction may have a partial opening in the short direction across the array when not compressed, but that opening has a silicone flap on one side of each air pockets' door. However, there is a flap is positioned on one side of each wall covering the door. When the pockets are compressed, air pushes on the flap side of the door and seals it seals tighter. The flap opens when pushed away from the wall, thereby creating check-valve pathways that transfer air preferentially along the short direction of the rectangular structure. When pressure is released, air is pulled in from the other side. Therefore the hot air is forced out when compressed, but then pulls cool air back in when release like a diaphragm. The flow directions alternate left and right for every other channel along the array of air pockets. If over compressed quickly, the bottom wall seals release so air just goes out in all directions so the pockets are kept safe from bursting under reasonable operating conditions.

In other embodiments, the device comprises a monitoring and control assembly including one or more light sensors placed in, on, and/or near the lighted window, facing toward a target surface when the device is in use so that the sensor(s) detect reflected light from the target, with the sensor(s) arranged to provide input to a controller circuit to adjust light intensity based on reflectivity, and/or to adjust the time of treatment. When one or more light sensors are placed in, on, and/or near the window of the LED array, facing toward the illuminated skin surface, the sensor(s) detect reflected light from the target. These sensor(s) provide input to a controller circuit to adjust the light intensity based on tissue surface reflectivity at the wavelength ranges being used, and/or to adjust the time of treatment. Multiple sensors sensitive to different wavelength ranges can be used for the detection of preferential reflected wavelengths of light and to permit manual or automatic adjustment of relative power to the mixture of different color LEDs.

Several common types of sensors may be made sensitive to specific wavelengths. Silicon sensors can be used so that multiple types of sensors may be packaged together. Optical filters may be used to allow sensors to preferentially detect spectra of interest. Example filters are available from many suppliers for specific notch wavelengths and for short pass or long pass filters include interference filters, gratings, and absorbing film filters, among others. Examples using a spectrum providing a 410 nm emission peak, a 650 nm emission peak, and a 810 nm emission peak would be short wavelength pass filters for below 420 nm, for 630 nm-680 nm n and a long pass filter for above 780 nm. These sensors can also provide and record data on the tissue or skin reflectivity at the designated wavelengths or wavelength ranges.

The device can comprise a monitoring and control assembly including one or more temperature sensor(s) that are arranged to directly or indirectly monitor a target surface temperature, e.g. skin temperature, and provide corresponding input to a controller configured to modify light intensity and/or treatment time of the device. These sensors provide information to a controller that can be used to modify the light intensity and/or treatment time as directed by the treatment clinician, physician, or by a predetermined formula in the controller or computer linked to the system. Infrared light sensors may be used and placed in or near the LED array, facing toward the target of the illumination that detects the temperature the target, provided a sensor is selected that is not affected by this light source's wavelengths. Many such products are commercially available. Surface contact thermocouples and/or other surface contact based temperature sensors may be used to monitor skin or tissue temperature. Likewise, either type of temperature sensor may also and/or alternatively be used for sub-dermal temperature measurement.

The device may be configured with the LEDs are positioned toward bundles of fiber optic loops or coils to concentrate light in a forward direction and comprising phosphors, quantum dots, fluorescent or phosphorescent dye, dye-doped fibers, and/or photonic crystal fibers to provide spectrum conversion. Coherent fiber laser light sources may be created.

The device in embodiments may be configured as comprising one or more piezoelectric, capacitive, inductive, or magnetostrictive transducers or motors to generate sonic and/or ultrasonic energy and/or vibration from, and/or in the vicinity of the output light as continuous and/or pulsed energy.

The light source may be constituted in embodiments to include electrodes to provide pulsed AC current to stimulate tissue surface and tissue locally under and near the light source.

In other embodiments, the light source may include 2 or more over 5 gauss magnets that can be permanent and/or electromagnets. Such magnets may be changed in polarity or positioned as desired mechanically or electrically. One or more electromagnets may additionally or alternatively be used and pulsed.

The light source device in embodiments may comprise one or more controllers that are programmably arranged to turn the device off at an end of a programmed time. Such controllers may be either imbedded and/or attached to the system and desirably can be programmed and turn the system off at the end of a programmed time. Over temperature switches may be provided and connected in series to turn the system power off in the event of overheating at 1 or more locations in the unit. One or more controllers may also optionally: turn off or on all or adjust the power to prewired portions of the LED array (modes) at designated times or resulting from other selected conditions being met: adjust the treatment time or power and mode conditions based on input from various light sensors monitoring parts of the patient's skin's reflected light spectrum, the patient skin or tissue temperature under the light, or other patient parameters; control any accessory features such as magnetism, TENS, and vibration; notify the patient and/or page a clinical attendant when the treatment time is about complete, or if certain selected conditions are met, or certain system failures occur. The patient may also turn off the system and page the attendant. The controller may communicate to one or more computers or databases. Other functions may be built in, e.g., preprogrammed functions including easy operation controls for home use without an attendant.

The disclosure also contemplates an LED array light source comprising channels arranged for peristaltic air pumping when the light source is bent and/or moved to increase convection flow in and out of the channels to effect heat removal from the LED array.

The light source device of the disclosure may comprise a cooling system configured to pump or suction air through an interior region of the device and/or for air over a heat sink in the device, and/or a water recirculation heat exchanger.

The device in various embodiments may comprise a diaphragm or bellows air pumped cooling system. The light source may use a diaphragm or bellows air pumped cooling system for a flexible LED array comprising: multiple LEDs mounted on a flexible printed circuit hoard (PCB) with heat-conductive material under and/or around each LED to provide a heat transfer to underlying heat sinks using, brazing, solders, or eutectic bonding, conductive composite materials, low melting point metal alloys, thermally conductive grease, and/or thermally conductive adhesive materials. A heatsink may be provided, comprising a thermally conducting material such as graphite, metal such as aluminum, plated or laminated metals, thermally conductive composites such as thermal conductive silicone or flexible carbon fiber, diamond particles, or metal fiber composites. These heatsink or LED module structures can be arrays of multiple rigid plates or bars arranged to effectively create a flexible tiled structure that is held together by webbing, screens, foil, thermally conductive tape, or other flexible structures. Multiple layers of these materials may be used. Fins, tubes or other known heat transfer structures may optimally be used to increase heat transfer area as long as they do not seriously interfere with the device operation.

A cooling system may be provided comprising a flexible molded or assembly of sheet material such as silicone or other polymers on the backside opposite the LEDs. This structure will have one or more electrical conductors in or on the polymer structured to perform as a bellows. The electrical conductor sheets to be covered or be coated with an insulating material to be minimally vertically conductive, and/or the opposing heat sink surface should be covered or coated to be minimally electrically conductive vertically. The heat sink or conductor placed over the heat sink may be used as a second electrode.

Standoffs may be provided between each pair of electrical conductors, placed periodically so that the plates generally remain apart unless forced together. These standoffs can be formed when molding one of either side of the bellows or added to the structure to the gap as separate components. An electrical change may be placed between these plates creates an electric force that can pull the plates together and push air out, and when release they can pull air in.

The bellows may be one or more large or long sections that can push most of the air out from between the conductors, can be a series of bellows that sequentially are activated by a controller to push air linearly in any selected direction, and/or can be configured as one or more smaller diaphragms or bellows that push part of the air in one direction due to check values built into the air part so air travels primarily in one direction for each channel.

If check value are used, they can be prefabricated and inserted into the channels during assembly, or the check values can be made as part of the structure when one or both sides of the channel are molded. The check vales may be simple flaps with a preferred direct and be blocked from reversing direction with molded in ridges. High dielectric constant materials such as epoxy/barium titanate coating composites are preferred over these conductor plates to reduce the required voltage. Magnets, conductive coils, and/or ferromagnetic materials may be substituted for the electrically conductive plate to provide an alternate motive force to these bellows. The device can also be configured with the chambers operating in the opposite polarity by the repelling the top and bottom walls of the chamber if the chambers are in a normally compressed state. This structure can be revised for lateral force driven pumping. Electrically controlled constricting or sheets fibers may also be used to compress or expand the diaphragm.

The disclosure also contemplates a method of light therapy treatment of a subject in need thereof, said method comprising generating a modified light spectrum output using a device according to the present disclosure, and exposing a body region of the subject to the light output thereof.

The method may be conducted, wherein the light therapy treatment is carried out to treat: joints and muscles for reducing pain and inflammation: wounds for improving the rate of wound healing; acne, rosacea, skin tone, and other dermatological conditions, to improve healing, and reduce the population of bacteria or fungus that are directly or indirectly photosensitive to the light spectrum of the light therapy treatment; muscles for enhancing regeneration of tissue after exercise or other stress; bone areas to repair damage and improve bone density; head, neck, spine, or other body areas, for pain and inflammation, for mood treatments, for reducing damage from brain injuries, or for increasing generation of nerve stem cell; veterinary subjects; photochemicals from food, herbs, and/or photochemical drugs for phototherapies; plants to enhance plant or algae growth or to control other plant functions selected from the group consisting of ripening, seed formation, and bud formation; or water and other fluids to activate photosensitizers for purification and/or antimicrobial and/or other pathogen treatments.

The method may be carried out to use a large area light source (area over 50 cm$^2$) in an area anywhere on the body using bracketed mechanical systems, straps, or adhesives, and/or other methods to keep the light source positioned correctly for a period of time. In all drawings hereinafter described, the textual portions of such drawings is to be regarded as set forth in this description, as incorporated in such description by reference.

Figure 2:
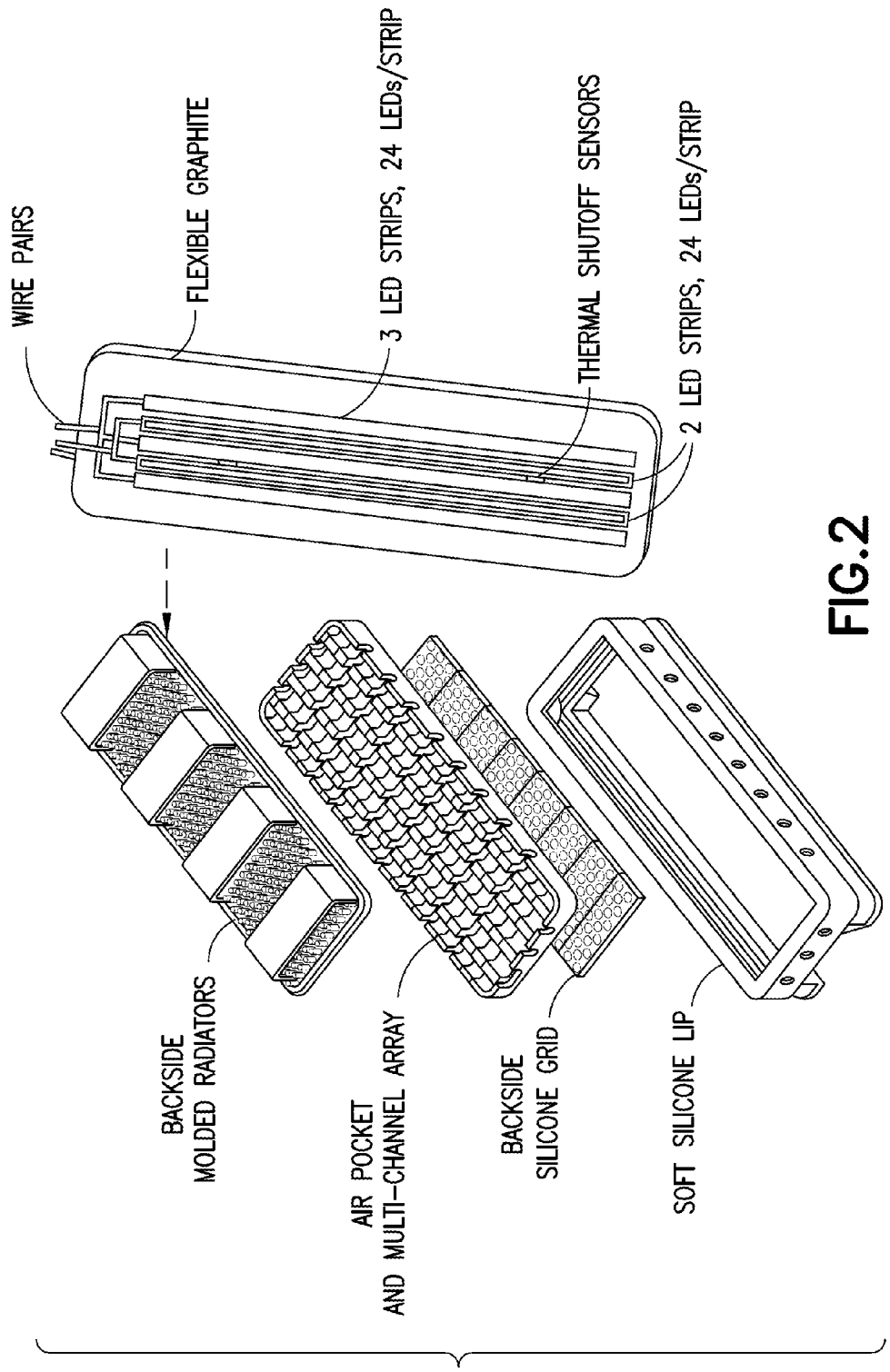
FIG. 2 is a disassembled bottom perspective view of the light therapy module of FIG. 1.

An example of one simple overall embodiment if this light therapy module is shown in FIG. 1. FIG. 2 provides a partial disassembly of this example light therapy light source. In this specific example embodiment, an assembly of flexible molded components (e.g., silicone rubber) holds heat sinks, silicone peristaltic air baffles, arrays LEDs with spectrum converting materials, and temperature limiters together. Not all aspects of this invention are depicted in this example. Microcontrollers and power supplies that attach externally and their optional wires are not shown. This simple spectrum converter example would emit a light spectrum with emission peaks 447 nm, 655 nm and at 835 nm, but unlike other light therapy systems, this system with only 2 type LEDs will also provide significant radiant power at all wavelengths between 440 nm-460 nm and between 590 nm-860 nm. In this example, light is emitted from the array of small window-like structures facing upward. The entire interior window array of small wells is all translucent silicone. These wells can hold lotions, gels, drugs, and/or refractive index matching materials next to the skin. There is also an array of larger size air pockets below these wells which act to reduce conduction heat transfer to the skin of the patient. Heat is easy to add or allow to increase, but a challenge to remove in small passive system with one side potentially pressed against the body without adding fans, blowers, pumps, and other additional features.

In the example provided in FIGS. 1 and 2, rows of a 120 high-power LEDs (~27 W power input at 12VDC or 24VDC) on flexible strips are longitudinally placed under these wells, and are therefore not visible in this view. Holes in the sides allow air to flow in and out of the interior of the structure to remove heat. Any bending or compression movements by the patient compresses the interior pockets and pushes warm air out, and then cooler air is pulled back in when pressure is released. However, the main heat removal radiators are located on the back side of the system that is better seen in FIG. 2. The backside of the light patch including the belt loops and optionally also the belt itself are all thermally conductive and help spread the heat over a large area for easy transfer to the air. Around the top perimeter of the device is shown an optional soft and flexible opaque lip that provides a soft surface against the skin and allows horizontal air flow when not pressed tight against the skin. This lip can flatten and allow the array of window—like wells to be pressed onto the skin if desired. This lip also blocks light leakage, which could potentially be annoying to users because of the very high light intensities this system provides. The light source contains a type of spectrum converters that have not been associated with this application and effectively uses extraordinarily high phosphors concentrations that are not considered practical along with novel concepts in backside heat sinking, forward heat control buffers, and peristaltic assisted hot air removal from the interior of the module. All of these are necessary for a good working device. In other embodiments of this invention herein, including the novelty aspects of the new spectrum converters are provided. The present device is a primarily non-coherent light source with over 70% of the output photon flux in the orange-to-near-infrared (ONIR) 595 nm-860 nm spectral range, where there are one or more high quantum yield (internal QY over 60%) spectrum-converting materials placed between the LED and the surface(s) to be illuminated, and one or more light emitting devices or other compatible light generators. These spectrum converter materials may be separate or be mixed into a single spectrum converter component.

Figure 3:
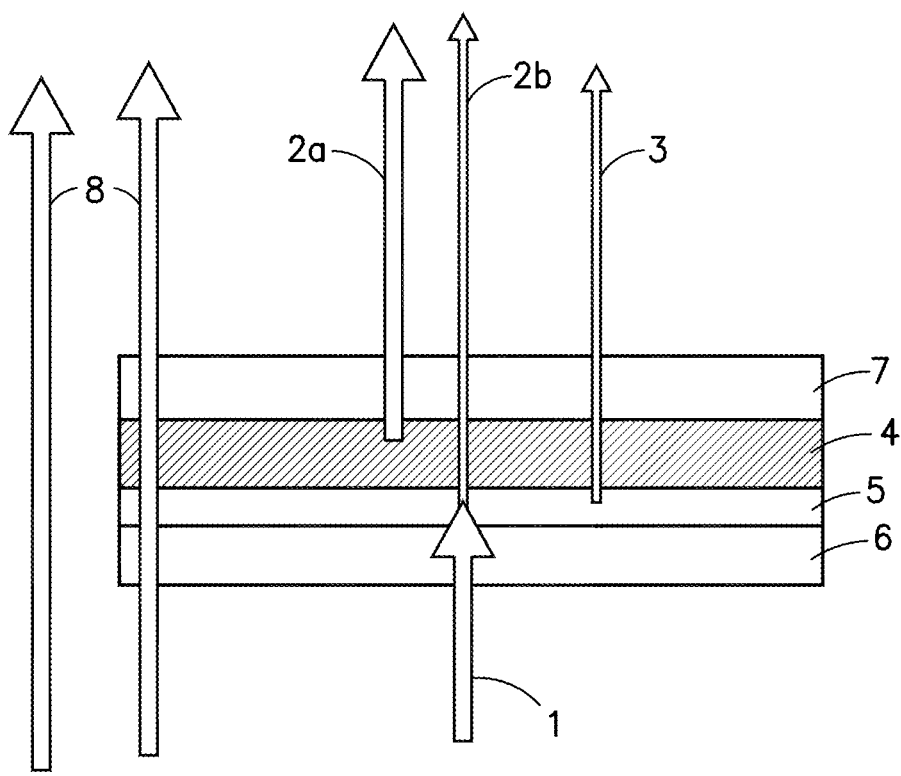
FIG. 3 is a schematic cross-sectional elevation view of a light therapy module according to another embodiment of the disclosure.
Figure 4:
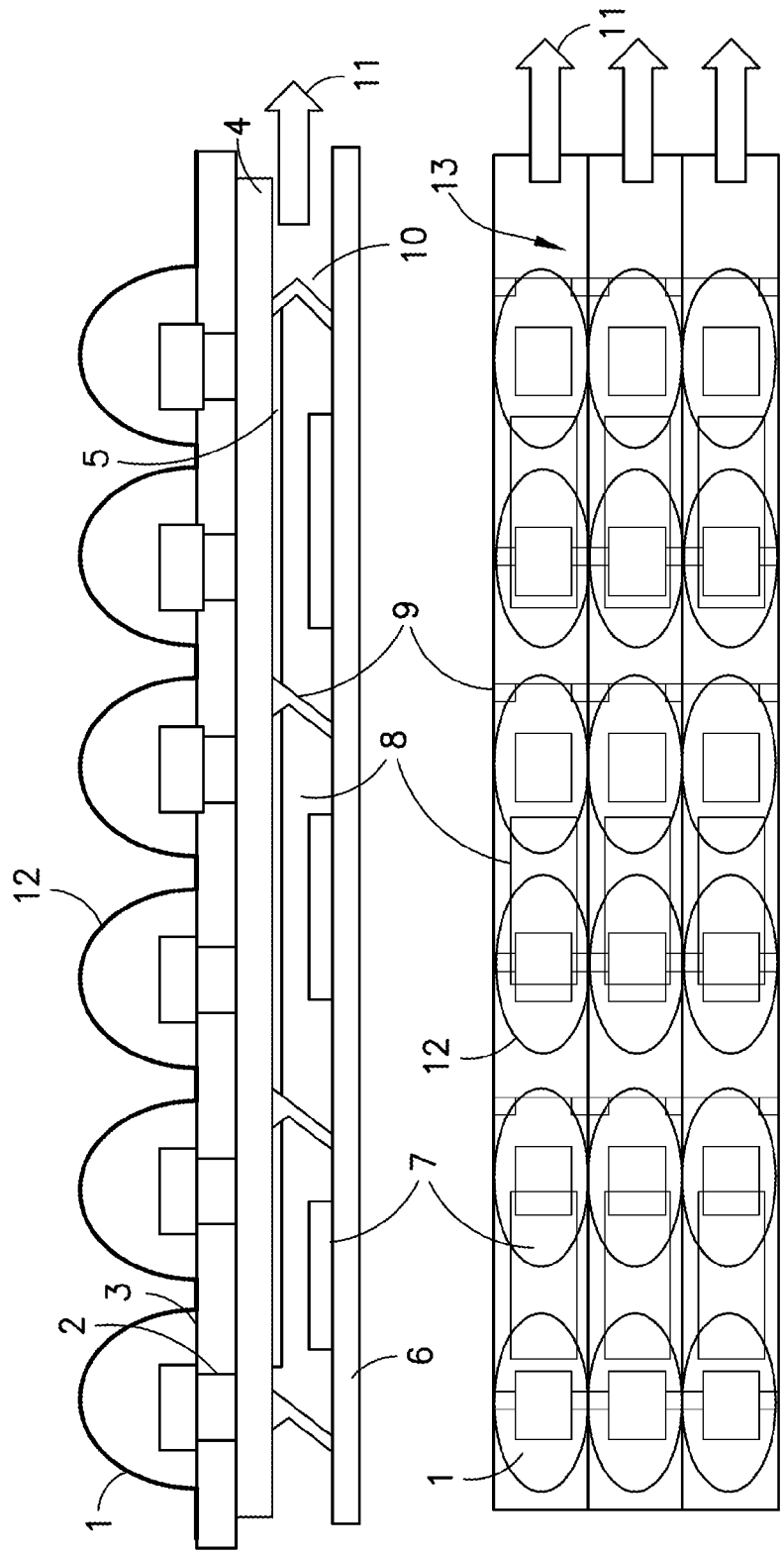
FIG. 4 is a cross-sectional elevation view and a top plan view of an electric field or magnetic powered bellows cooling assembly for an LED lighting device, according to another embodiment of the disclosure.

FIG. 3 provides a simple diagram showing the function of the 1 and 2 stage spectrum converters. FIG. 3 also shows the concept of mixed light where not all of the light needs the spectrum converted. Some therapy lamps may have switchable modes for purposes permitting some spectral and/or radiance modes to be those discussed in this document, but other modes may also be possible. Light source modes supplementing the converted light modes with significant radiant emission peaks within the 760-860 nm spectral range are considered very important.

In the present invention, we will generally use the term "LED" as a generic acronym placeholder for "Light Emitting Device," encompassing all initial solid state light sources. The preferred initial light sources for most applications are light emitting diodes (also commonly known as "LEDs") or semiconductor diode lasers but additional options include but are not limited to other lasers, organic light emitting diodes (OLEDs), electroluminescent, and/or other solid state light-emitting devices.

Other light sources which can also be used as LEDs in all of the embodiments, include but are not limited to gas lasers, liquid or gel lasers, solid state lasers, fiber optic lasers, electroluminescent, cathodoluminescent, halogen lights, gas discharge lamps, plasma light sources, fluorescent lamps, quantum dots, and other liquid, gas, vacuum, and/or types of visible or near-infrared light sources available now or in the future.

In the present invention, the term "spectrum converter" consists of one or more photoluminescent materials in a structure that permits light to be absorbed and re-emitted efficiently. The spectrum converter can also be called a color converter. These spectrum converters must collectively convert light emitted by the to-be-converted LEDs into ONIR light, and the converted light output must contain photons with wavelengths covering the majority of the ONIR spectrum (595-860 nm).

The initial LEDs, LEDs plus phosphors, or other light generators may be either broad spectrum or narrow spectrum sources, as long as those light generators to be spectrum-converted can significantly stimulate the spectrum conversion portions of this device meeting the photo-luminescent light absorption and emission criteria described herein.

In a preferred embodiment of the invention, at least one of the spectrum converters in each LED with spectrum converters must provide a larger than 100 nm spread between the longer and shorter wavelengths where 10% of peak emission intensity occurs. In one embodiment of the device structure, this can be accomplished using a single photoluminescent material such as a 650 nm oxynitride or nitride phosphor, and in another variation this could be accomplished by using multiple narrow emission spectrum photoluminescent materials such a matrix of quantum dots converters with optional phosphors or dyes mixed in and or layered on or over the device.

An embodiment of the present invention incorporates use of a dye as a spectrum converter. In this discussion, we use the term "dye" to refer to fluorescent or phosphorescent materials that are mostly distributed at a molecular level in solutions (e.g., polymers, sol gels, low temperature glasses, liquids or gels, and other translucent materials in a wide variety of shapes). Dyes may aggregate into groups of molecules, remain separate in the medium, and frequently contain some combination of both dye aggregates and non-aggregated dye molecules. The definition of dyes in this patent filing is generalized to refer to all photo-luminescent organic dyes, organic pigments, primarily organic particles and nanoparticles, and/or bulk photo-luminescent materials.

Spectrum converters are not new or unique. However, the phosphors, dyes, and QDs in this invention are used far outside of the conventional and published ranges and in this different applications space and in different configurations with surprisingly good spectra and light output efficiency results when used with these classes of converter materials, these LEDs in these configurations, with this cooling of the devices and materials, at these thickness, concentrations, input light radiance, and with these unique spectral input and output objectives. We found that we only degraded the output QY by about 5-10% if we increased the color converter thickness by 1.5-2.0 times and increased the phosphor concentration by 2.5 times what we previously considered to be upper practical limits. Over 70% light absorption of incoming blue or violet light by a phosphor or dye in a spectrum converter requires these very high phosphor layer thickness and concentrations when compared to conventional uses. It is this very high >12% total phosphor concentration that is unique and still provide a reasonably high QY if done correctly.

The color converter concentrations and % absorption are far outside the conventional operational modes. Specific reference is to the practice with nitride and oxynitride 5-25 micron phosphors on 3528, 2835, 5050, 5056, 1 W, and 3 W under 450 nm dominant peak emission LEDs We observed an over 10× increase in overall radiance capability per unit area. The 3-way cooling, short optical path length (<1 cm), airless coupling of light into the tissue, and with reflectors being just a few millimeters away from the skin redirecting much of the scattered or backscattered light from the tissue and skin back into the skin all appear to contribute to the enhanced capability to deliver red and near-IR light into the skin.

We surprisingly found it was possible to obtain as much light radiance per unit of system cost at good power efficiency in the specific spectral ranges of interest this way in the 640-720 nm range as with conventional single color LEDs or lasers, and then we can use the additional "almost free" orange-to-red 590-640 nm light, some of the blue and/or violet light, another >720 nm near-IR energy to really provide multi-purpose system benefits for both shallow and deep tissue treatments using basically the same configurations, especially using the free added orange spectral region.

Few serious researchers have even tried the color converter approach for light therapy other than for some relatively low radiance white light alertness tests (but high-radiance for "bright" vision is extremely low-radiance for deep tissue light therapy and the spectral ranges are totally different). This is because lasers with narrow bandwidths have been preferred for lab experiments on light therapy, and only in the past few years have LEDs really started to take hold due to their plunging cost. Also, multiple recent studies showed similar therapeutic results between LEDs and laser diodes for many conditions. During the last 2 years, it has also begun to become apparent that the therapeutic windows are probably quite wide +/−30-50 nm for several light therapies (especially for pain and inflammation related that may be as wide at 640 nm to 900 nm depending on the target depth and treatment conditions) due to multiple studies providing similar result in different spectral ranges. Those wavelengths are all included in this spectrum, and at high radiant intensities. If all of these wavelengths ranges are really as effective for pain, inflammation, and accelerating tissue repair, then the radiant total power out of these new light sources and the radiant power absorbed into the tissue will make these type devices far more effective, or at least as effective with shorter treatment times, than anything else available today even at 10-20 times the cost.

For Lumogen F 305 dye from BASF and the newer OR perylene-related class dyes discussed herein, we found that at 0.15-0.50 mm thickness layers at, over 70% absorption could be achieved with over 85% conversion efficiency and more than sufficient photostability for these unique type products when used in conjunction with these phosphor color converted 630-670 nm high converted light beams at very high radiant light intensities.

A preferred embodiment utilizes very stable, low cost organic dyes that are soluble in a variety of polymers that provide the wide spectral range desired and very-high efficiency emission in the deep-red to near IR range. These new dyes are perylene derivatives with peak emission at approximately (depends on medium, batch, and final operating conditions) 615 nm, 645 nm, 670 nm 775 m, and/or 820 nm. Previously known existing perylene dyes may also be integrated into embodiments of this new invention, including but not limited to dyes such as BASF Lumogen Red 305 (600-610 nm emission peak).

Another embodiment of the spectrum converter of the present invention incorporates use of phosphors as the spectrum converter. This term is generally used to refer to mostly inorganic photo-luminescent materials (fluorescent or phosphorescent) that are used as nanoparticles or small particles that appear like a fine or granular powder before mixing into solutions (e.g., polymers, sol gels, low-temperature glasses, liquids or gels, and other translucent materials in a wide variety of shapes). In this discussion, for simplicity we generalize the use of "phosphor" to cover all particle based photoluminescent materials which includes but is not limited to inorganic phosphors, inorganic photo-luminescent pigments (e.g. Egyptian Blue), quantum dots, nanocrystals, and other color converting materials.

A preferred embodiment utilizes several new violet and blue light absorbing, deep-red emitting oxynitride or nitride phosphors that provide part of the desired ONIR spectrum which can work synergistically with the new organic perylene derivative dyes, and not just by being additive. The peak emission wavelengths of 2 of these new phosphors are 650 nm and 670 nm. Variations of these phosphors with similar spectral characteristics are available from multiple suppliers.

In addition, the present invention also incorporates the optional use of quantum dots or other nanostructural spectrum converters, to allow further customization to the output light spectrum for light therapy. Quantum dots are nanoparticles or microparticles with multiple layers or atoms or molecules around a core, instead of single composition crystal particles like in most phosphors or coated phosphors. As photoluminescent materials, they behave similar to phosphors, but can be more efficient and highly selected quantum dots of the same structure can exhibit more narrow emission spectra unless there is a specific reason to separately refer to QDs. Unless there is a specific reason to separately refer to quantum dots, quantum dots will usually be incorporated into the "phosphor" category for most references herein.

While these quantum dots are narrow spectrum emission and may be more expensive than other alternatives, quantum dots are available at several peak wavelengths in the red spectral range, and multiple quantum dots can be made with a variety of wavelengths and mixed to create a virtual broad spectrum light source. Using small amounts of these quantum dots can allow fine-tuning of the spectrum for the most demanding applications without serious cost implications.

The present invention provides for a wide variety of combinations of phosphors, quantum dots, and/or dyes as photoluminescent spectrum converters.

In the present invention, other wavelengths of light may also be present in the light source output spectrum at up to 15% of the total output photon flux from the portion of the light source that converts light into all or a large part of the ONIR spectrum. Light sources producing other wavelengths, with or without spectrum conversion, may be used to further supplement the intensity of selected wavelengths of light.

The present invention anticipates use of principally-ONIR spectrum-converted LEDs and mixtures of ONIR spectrum-converted, non-ONIR spectrum converted LEDs, and non-converted light LEDs.

The present invention also incorporates a "matrix," sometimes referenced as "medium." Either term refers to a material that is mostly translucent to the absorption and emission wavelengths of the photoluminescent materials placed in that material. These medium materials can be coatings, sheets, bulk materials, molded or otherwise shaped materials, or liquids in a cavity. These materials may consist of organic and/or silicone polymers, glasses, crystals, microstructured or nanostructured arrays, multilayered structured materials, inorganic composites, inorganic and organic composites, sol gels, liquid crystals, and many other materials. The medium materials may be in the form of solids, semisolids, chalcogenides, gels, liquids, liquid crystals, and/or combinations thereof.

The thickness of the translucent matrix and spectrum converter materials in this invention can vary from a micron or less to up to many centimeters because the optimal and photoluminescent material concentration thickness depends on the specific materials selected and the final spectrum objectives in a specific design. Typical spectrum converter thickness will be in the 0.1 mm to 5 mm range, unless the converters are in or part of single or bundled optical fibers where the spectrum converter material concentrations will typically be lower and the optical path lengths through the spectrum converters may increase substantially. It is anticipated that these are design issues that can be predicted and experimentally adapted for this invention by engineers or scientists with a basic understanding of photoluminescent phosphor and dye technologies, published literature, and by using the concepts presented herein.

Very thin light spectrum converters may be made using pure or very high concentration (>70%) layers of dye and/or phosphor material without a matrix material, or very little matrix material, as long as the films have uneven surface texture or are discontinuous to reduce light trapping effects and provided aggregation of the dye can be controlled as to not greatly reduce its efficiency.

The dye and/or phosphor concentration required to convert a certain percentage of the input light at a given wavelength and intensity reduces almost proportionally within a given converter matrix volume.

The type of matrix used to contain a dye can change the stability, absorption, and emission spectra, or even quench the photoluminescent properties. While typically less pronounced, optical characteristics of phosphors, quantum dots, and other spectrum converters can also be affected by different medium. Other materials discussed can work together, but may require different thicknesses and concentrations or other additives. Multiple types of dyes, phosphors and other spectrum converting materials in a matrix can interact, effecting relative concentrations, stability, photoluminescence and other optical or physical characteristics.

Organic dyes can offer less scattering losses because they can be mostly distributed at a molecular level, and can provide higher quantum yield than most phosphors. Lower concentration of dye in proportionally thicker films tends to reduce aggregation risk and improve conversion efficiency and photostability. Thicker converter medium are heavier and tend to be less flexible.

A preferred structure of the invention is provided where the photoluminescent materials in the spectrum converters are arranged so the "converted-spectrum" light exiting one spectrum converter has a predominantly longer wavelength spectrum than the absorption spectrum of the spectrum converter the light then enters. Therefore, primarily unconverted light passing the first converter is absorbed and converted by the second converter, thereby providing higher overall energy efficiency. This structure can be applied to 2 or more sequential color converters.

Another preferred embodiment is that the spectrum converters following the first color conversion pass through a minimally scattering spectrum converter such as a dye or quantum dot.

Another preferred embodiment of the structures in this invention is that a matte surface texture, other surface patterns or textures (arrays of mini or micro lenses, basketball-like bumpy surfaces, or other surface modifications), or structural discontinuities in the spectrum converters be provided to minimize light channeling and capture related losses in the spectrum converters.

Index matching materials can be placed between sequential spectrum converters for eliminating air gaps between the spectrum converters and between other layers of translucent material the light path is expected to pass through can be used to reduce light coupling losses. Also, under 1.5 refractive index soft translucent silicone (at or under 30 Shore) can be pressed against the skin or other tissue to provide enhanced light coupling.

The use of reflectors around and between the LEDs should be used to redirect light toward the surface to be illuminated.

One embodiment of the invention is a light therapy device consisting of multiple layers of all closely index of refraction matched phosphor and/or quantum dot and/or nanoparticle color converters, as previously described, that also matches the refractive index of human or animal skin. The embodiment can also be soft and conformal.

The use of index coupling materials in contact with the skin can further increase the light transmission into the skin, as can minimizing the occurrence of air gaps between the skin and light source. The nominal index or refraction of living skin for the 650-850 nm range, even taking racial or heavily tanned skin pigment differences into account, is approximately 1.4. Extreme index of refraction variations still tend to still be within the 1.33-1.44 range. Several solutions can be used for index matching including ~25% gelatin-water mixtures, ~30% glycerine water mixtures, ~35% sugar (e.g., sucrose): water mixtures, and several oils. Silicone gels have recently become available that can be customized to a wide range of refractive indices including 1.40, and these are non-liquid, highly-conformal and contact safe materials.

The present invention specifies that the use of the customized 1.4 refractive index silicone material (or other 1.4 refractive index polymers) used as a matrix materials for phosphor and/or quantum dots spectrum conversion materials can be close to an index of refraction of 1.4 +/−0.5, to minimize light losses due to refractive index changes from the exit of the LED to the skin. Minimal losses due to air spaces between the light therapy device and skin can also be achieved with a conformal or body contoured light source device like those described in this patent application and soft silicone gels. Translucent, food grade, silicone with hardness under Durometer 20 is preferred for the portion of the silicone facing the skin, unless pressure is used to compress the light therapy devices against the skin, an index matched liquid or gel interface to the skin is provided, or a body shaped rigid material, such as low index glass, is used.

Selecting thin, low index of refraction polymer for the dyes and having only a single transition in and out of one color converter with minimal occurrence of air gaps in the light path is also a viable energy efficient structure.

The LEDs in this application are considered to be discrete, although OLEDs and electroluminescent devices could be fabricated as 2D panels. Many discrete LEDs can be laid out to form 2D arrays. The LEDs can be a screen matrix layout, serpentine layout, and/or formed as multiple rows and/or columns of LEDs.

For rectangular and many other shape 2D LED arrays, rows of LEDs laid out as linear strips are a preferred embodiment. (2836, 5050, 5060, or 3528 light emitting diodes are examples of LEDs that can easily be surface mounted onto flexible printed circuit boards strips using automated equipment at low cost.) These LED strips can be connected at the ends and powered at low voltages. A typical LED strip drive voltage is 12VDC, but other LED strip drive voltages can be purchased or designed. The number or LEDs per 10 cm length of LED strip can be varied, although 12 LEDs per 10 cm long 3528 strip or 6 LEDs per 10 cm long by 1 cm wide 5050 LED strips are considered standards. Twice this number of these LEDs per unit length are now commercially available (e.g., 120 5050 LEDs/meter for about 27 W/meter).

LED strips are frequently coated with translucent silicone, polyurethane, or epoxy to be made more waterproof. The preferred invention provides that these coatings can be made using customized ~1.40 index of refraction silicone gel, and that photoluminescent phosphors or quantum dots can be placed within that matrix. 0.46 to 0.56 index of refraction polyurethane is also a good choice in this invention that is very low cost, but with poorer light transmission coupling into the skin. Other LED coating materials exist or are being developed that could be substituted, and materials can be layered to provide step graded index where the bulk coating material could be low cost, but then multiple layers of different thinner material coatings using "effectively" graded index or refraction and scattering properties to improve light transmission and light coupling to the skin. Other less flexible coatings or polymers could be used on top of the LED devices, so flexing the LED strips would not be significantly impeded. This would permit dyes to be used directly on the LEDs in these films (such as acrylic) either above or in a silicone coating.

An embodiment of the present invention incorporates pulsing of the LEDs, if desired, as a way to modify the therapy or to reduce the average power to the LEDs and thereby reduce the nominal intensity without changing voltages. The LEDs can be modulated or switched on and off at 4-over 100 million cycles a second depending on the drivers and type of LED, and/or at other frequencies and duty cycles. 8-15 cycles per second is a preferred range for neurological therapies, but modulation frequency is less important for other therapies. Very high frequency modulation can be useful for photoacoustic imaging, especially when coupled with photoacoustic reporter materials such as high extinction red and near-IR cyanine dyes, and may have other uses.

The discussion now provides several specific examples of preferred embodiments of the present invention.

Referring now to specific Embodiment 1, there is provided a light source, comprising an array of two or more LEDs and/or OLS, where at least one of the LEDs and/or OLS has one or more materials containing photoluminescent phosphor(s), dye(s), and/or OCSTs that spectrum-shift most of the light energy emitted from the selected LEDs and/or OLS into an emission spectrum substantially within the ONIR wavelength range. Different spectrum-converting materials may be mixed or sequentially placed in the light path so that 1, 2, or more different spectrum converters are present in the light path of at least half the collective initial LED light output.

Still referring to Embodiment 1, the spectrum converter can be a phosphor or quantum dots mixed into clear silicone or other matrix material placed in the proximity of, or touching the LED light-output surface at a concentration, thickness, and area that can convert 50% or more of initial LED light into broad spectrum ONIR light with a emission intensity dominant peak at 620 nm or higher. In the example provided, we use a broad emission spectrum commercial phosphor ~650 nm peak emission nitride or oxynitride red phosphor with an internal QY above 70% such as can be commercially obtained. BASF 305 red dye provide absorption in the blue-green-yellow spectral ranges with a peak emission near 610 nm and an emission tail past 750 nm. We have also found that an even deeper red shifted spectrum can be obtained using a 0.01%-0.3% concentration of a special new 670 nm peak emission Perylene dye placed over the red phosphor coated LED above. An additional phosphor in this range is LED NR655, which is a 655 nm emission peak nitride phosphor from SHANGHAI RURAL INDUSTRIES CO., LTD. In China.

The amount of blue or violet light left unconverted depends on the exact design parameters used and needs to be experimentally established for each device and phosphor matrix parameters used. A second phosphor such as Intermatix 670 nm phosphor, single or multiple near-IR emitting quantum dots from QD Vision Corporation or Nano Optical Materials (there are also other sources), or near-IR emitting phosphors from Taylorlux or Materion can be mixed into Material 1 or added as a second material in the light path to further extend the light emission over the spectral range over the Near IR range. The spectrum of this embodiment can also be supplemented with one or more unconverted LEDs with peak emission in the upper near IR range such as 780 nm, 810 nm and/or 840 nm LEDs. Because of low cost manufacturing tolerances and a wide useful biological response in the range, this is effectively a preferred 770 nm-860 nm range of dominant spectral peaks.

The light source device described for Embodiment 1 is unique because of the specific "broad spectrum" ONIR light spectrum created by the synergistic interactions of the LEDs and/or OLS and the special broad spectrum converters. The light emission spectrum has the important unique capability of providing light energy covering all or almost all of the ONIR spectral range that can provide therapeutic light energy benefits to shallow through to deep tissues, but also providing light intensity peaks to address specific important therapy or biological process. This is done in more cost effective way than previously disclosed. The use of efficient solid state Light Emitting Diodes or laser diodes is the preferred embodiment of this invention.

A specific example, designated as Embodiment 2, has an additional light conversion material placed in all or part of the light path, consisting of one or more over 60% quantum yield dyes in an inorganic or polymer matrix such as polycarbonate, impact resistant acrylic, or PVC. Polymer matrix mixtures are anticipated and can be beneficial. For most preferred embodiments 0.05-5 mm would an optimal range.

Selected perylene derivative dyes have much higher photostability, higher QY, and ease of integration into a wide range of light converters than almost any other red or near-IR spectral range organic dyes. Even though photostability is lower than phosphors, this can be managed in many medical applications for the life of many products or the conversion material can be changed out as part of routine maintenance. The absorption and emission characteristics are needed for useful ONIR spectrum.

The present invention incorporates inclusion of two new perylene derivative photoluminescent dyes which provide broad spectrum light emission with emission peaks at ~775 nm and/or ~820 nm. These emitting dyes are important examples of new near-IR dye with broad band peak emission at about 775 nm and 820 nm respectively. This new 775 nm emitting dye is used as the spectrum converter in Embodiment 2 in which light absorption in the violet and in the 595-720 nm range uniquely allows single-step conversion to a broad near-IR spectrum center around 775 nm from violet, and then double conversion from red light. If this dyed material is only placed in the light path of unconverted violet LEDs, or over orange-red emitting LEDs (630 nm), the overall light source efficiency can be further improved and tailored. Additional combinations and variances of these basic structures are anticipated. One or more types of QDs with emission peaks in the 760 nm-860 nm spectral range can be substituted.

Still referring to the Embodiment 2 example, a specific example of the added spectrum converter material would be a ~0.2 mm thick flexible and transparent polycarbonate sheet or other suitable polymer with 0.1% 775 nm dye for the subsequent spectrum converter. Similar concentrations of QDs may also be used.

Still referring to Embodiment 2, the subsequent spectrum converter can alternatively contain both the 780 nm and 820 nm derivative dyes, phosphors, and one or more type QDs with emission peaks in the 760 nm-860 nm spectral range. A concentration ratio of 0.08% 775 nm dye and 0.06% 820 nm dye can be used to greatly increase light output over the 740-860 nm range. A 2% addition of poly vinyl chloride (PVC) to the polycarbonate during the converter sheet fabrication can improve the quantum yield for this dye and/or the 820 nm dye.

Still referring to Embodiment 2, the subsequent spectrum converter may also contain one or both of these new perylene-derivative dyes, the older fluorescent perylene dyes, and/or one of more other spectrum converters such as phosphors.

It should be noted that the afore-mentioned embodiment, and its variations, is very unique as it uses selective light absorption and dual light emission to optimize ONIR light output. These spectrum converters are not just mixtures or combinations. Rather, these are highly interactive, synergistic materials that work together uniquely. The absorption and emission curves plus non-photon energy transfers provide higher performance and energy efficiency than one knowledgeable in the arts would have anticipated.

An Embodiment 3 of the spectrum converter is comprised of a light source consisting of an array of two or more LEDs with principal light output in the 390-490 nm range, where at least one of these LEDs is covered by one or more layers closest to the LED containing photoluminescent phosphor(s) and/or quantum dots so that over 50% of the output light spectrum from the converted LED(s) is within the ONIR spectral range. Additional spectrum-converting layer(s) using fluorescent dye(s) or quantum dots then converts most of the light energy exiting the first layer(s) into the ONIR spectral range, and/or into a longer wavelength portion of the ONIR spectral range. This device's output light from the spectrum converter(s) may intentionally contain up to 40% light in the violet and/or blue spectral range with >60% light in the ONIR spectral range. Light source designs with over 99% of the photons in the ONIR range are achievable with this structure and appropriate photoluminescent material concentrations and layer thicknesses.

Embodiment 4 of the spectrum converter: According to another aspect of the present invention, there is provided a light source, comprising an array of two or more light-emitting diodes, where at least one of the LEDs is covered by one or more layers containing fluorescent dye(s), phosphorescent dyes, photonic crystal-like arrays, and/or quantum dots to color-shift yellow, orange, or red (580-650 nm) light energy from LED(s) into the ONIR wavelength range and/or into longer wavelengths within the ONIR spectral range.

In any of the above-described embodiments of this invention, additional LEDs (whether spectrum-converted or not spectrum-converted), may be added to the apparatus to increase the light intensity in certain portions of the light spectrum. For example, if the light output from the spectrum-converters and LEDs has a dominant peak light intensity at 650 nm, then the light output at 800 nm may be lower than desired for some LLLT applications, even though example phosphor and fluorescent converters with 650 nm peak emission intensity will provide some photons 150 nm above the peak output. Additional LEDs can be added to increase intensity in the longer wavelength portion of the spectrum. For example, 665 nm, 680 nm, 720 nm, 735 nm, 760 nm, 780 nm, 810 nm, 820 nm, 840 nm, 850 nm, and/or even up to 940 nm dominant peak range LEDs may be added to the light source. Longer wavelength peak emission color converter layers can also be used on some or all LEDs to shift the average spectrum from shorter to longer wavelengths via a spectrum-conversion cascade. Violet or blue LEDs could also be added without color converters to create spectral peak(s) in the short wavelength range.

In these embodiments, spectrum-conversion may be accomplished either by having the incident light pass though the translucent spectrum-converting medium for one of more of the layers placed (1) between the light source and the surface to be illuminated as sheets or coatings, (2) the translucent film(s) containing the photoluminescent materials on or over flat or shaped reflective surfaces, (3) the photoluminescent materials may be imbedded in fiber optics (e.g., polymer with low index of refraction coating), and/or (4) as optical structures such as prisms, lenses, or lens arrays.

As a further specific example of the invention's previously described Embodiment 1, a simple 1 layer converter design includes a VIB LED (e.g., 430 nm or 450 nm dominant peak) beneath a 0.3 mm thick mat-finish impact resistant acrylic film containing a mixture of 610 nm and 670 nm perylene dyes (0.2% concentration for each component dye, total 0.4% concentration). BASF red 305 perylene dye also provides for a reasonable example dye for this embodiment.

This type combination of dyes in this concentration range can absorb and convert enough of the 430 nm light to provide an output light spectrum with over 70% ONIR light with a 670 nm peak light, and retain a VIB light peak LEDs. The 610 nm dye absorbs much of the VIB light and efficiently transfers much of its energy to the 670 nm dye. This example device using the 430 nm LEDs would be useful for many skin therapies and deep tissue therapies, but also would be useful for plant growth and blooming or ripening if powered by 450 nm LEDs. This example can be made using two 0.22 mm thick layers of dyed film with the 610 nm dye closest to the LED and then the 670 nm dye may be optionally placed over the 610 nm dyed film. Alternate polymer films such as polycarbonate or PVC may be used and other spectrum converter dyes or phosphor may be inserted as extra layers or mixed in the film.

A further example of the invention's Embodiment 2 uses a 650 nm-peak emitting phosphor suspension in a silicone polymer coating placed over LEDs with a significant amount of its light emission within the 400-435 nm spectral range. The concentration of the 650 nm phosphor in the silicone is approximately ~11-20% (weight %) in the 0.1-0.2 mm thickness range. This spectrum-converter on this type violet-blue LED can provide light with over 70% of the light within the ONIR spectrum. Optionally, then a 670 nm dominant peak-emitting perylene dye at ~0.25% concentration (weight %) in a ~0.2 mm thick, textured (e.g., mat-finish or other light scattering surface) acrylic, PVC, or polycarbonate film is placed over the 650 nm-phosphor converted LED. The combination of these 2 spectrum conversions can provide light emission spectrum centered in the 645-675 nm spectral range with less-than 15% of the peak emission intensity for wavelengths under 610 nm. An alternative is to mix 650 nm phosphor and 670 nm phosphors together or to use 650 nm phosphor with 670-700 nm QDs. 1-15% of the photons in the output spectrum can remain in the violet range if anti-microbial functionality is desired. Alternatively if using much higher collective phosphor, dye, and/or QD concentration, almost no violet or blue light may be left in the spectrum depending on the application using thicker or higher concentration phosphor and/or dye in either or both of the polymer film layers. Additional layers of spectrum converting films with longer peak emission wavelength dyes or quantum dots may be used to further shift all or part of the output light spectrum to longer wavelengths.

"Low-temperature melting Glass" (LT Glass) can be used as a matrix for certain perylene derivative dyes if the glass transition temperature is below 450° C. For phosphors in glass, the glass transition temperature can be much higher and can include many types of glasses, depending on the phosphor used; however index of refraction matching between the glass and phosphor grains becomes more important.

LT Glass matrix: Several perylene fluorescent dyes and/or phosphor and dye mixtures can be inserted into a low-softening-temperature glass to provide spectrum converters. Example sources of translucent low-temperature glass (powder or solid): Low-melting Glass Powder (TF-100H, TF-100HF) from Taizhou Sunflex Industrial Co., Ltd. In China, Satake Glass Company in Japan (leaded or non-lead glass), and ARTCO Inc. in the USA). It is non-obvious that organic fluorescent dyes can be mixed into glass and be made highly active. This is unique to this perylene class of organic dye. Phosphors mixed in glass are known, but the use of high-temperature capable organic fluorescent dyes into glass is new. The unique class of perylene high stability, high temperature derivatives dye can be mixed into a glass powder before melting, or into molten glass. A low oxygen and moisture environment is preferred during mixing and melting (e.g., nitrogen, argon, and/or vacuum). Mixing can be accomplished using agitation (vibration, ultrasonic, shaking, spinning, pumping, and/or stirring). The mix can be prepared at above the LT Glass melting point (prefer 450-550 deg. C. for under 1 hour). The molten glass can then be placed directly over LEDs, and/or molded into shapes, placed in droplet arrays on surfaces, or otherwise formed to make flat or curved filters, lenses (including microlens arrays), and other shapes. Glass droplets or other molded glass shapes may be placed onto other transparent or reflective materials or other structures to diffuse or focus light. Dye concentrations between 0.01 and 5% are considered useful depending on the application. 0.15-0.35% (weight %) is an example optimal range for some converter medical applications using the 670 nm emission peak perylene dye for blue to red-orange light sources. 0.1-30% phosphor (weight %) may be added to the dye is starting with UV, violet, or blue light sources. These spectrum converter materials may be designed into multiple layers or mixed into the glass. Films or coatings (polymer or other translucent materials) of dyed, phosphor, or other color converter layers may be added as layers.

Additional dye options include Rubrenes, rhodamines, cyanines, and many europium complex dye derivatives which have usable characteristics for these new device structures in translucent polymer material matrices, although these dyes are inferior in photostability and quantum yield to the referenced perylene dyes.

Orange-red LEDs with primary dominant peak light emission in the 610-630 nm range can be efficiently converted to provide light with dominant peak emission in the 660-680 nm range and with over 70% of the output light spectrum for most published ONIR skin treatments that do not require UV or VIB spectral range light. The NIR tail above 680 nm provides improved depth of tissue penetration by NIR light. In this example, a ~670 nm perylene derivative fluorescent dye in a suitable translucent medium is used (e.g., 0.15-0.35% dye in 0.10-0.35 mm thick polycarbonate (PC), polyester (PE), acrylic, polyvinyl chloride (PVC), and/or other translucent medium such as LT glass). Alternatively, 640-700 nm phosphor or QDs may be used over the UV, violet and/or blue LEDs. These orange-red light converters and the prior violet-blue light conversion devices may be mixed together in the light source and/or combined with other LED types to create lower cost, high energy efficiency, and improved LLLT and PDT activating light sources. Also, the >20% of the output photons in the >700 nm range are known to enhance plant ripening and/or blooming while the remaining broad-red spectrum light provides the energy for accelerated plant growth. A small amount of added violet and blue light can also provide for a versatile horticultural lamp. The violet-blue spectral range light can be provided by mixing Example 1 and Example 2 device types, and/or by adding supplemental VIB LEDs to either light source.

In another even more specific example embodiment of this invention, violet LEDs with a significant (>10%) amount of the LEDs' light output being in the 400 nm-465 nm spectral range are used to drive the above color converters to provide a unique light spectrum for skin treatments with both antibacterial and healing properties. The output spectrum (photon ratio as %) for this embodiment of the invention is >65% ONIR light and 2-35% violet light in the 400-435 nm range. This output light spectrum can be obtained without the use of mixed LED types. Some high value uses are for acne treatments, skin care and rejuvenation, wound healing, and PDT using mixed short and long wavelength photosensitizers.

In embodiments of the present invention, multiple dyes and/or phosphors or quantum dots may be mixed or layered to provide many different ONIR range spectra that can be optimized for specific uses. For example; an intensity-vs-wavelength spectrum light can be generated efficiently from UV, violet, blue, and/or orange LEDs over ONIR ranges such as with less than 30% variation from the peak emission intensity covering the 620-690 nm range using the example materials discussed. A significant amount of light can be generated by the "tail" of the example dye and phosphor emission spectrum providing up to 5% of the peak light emission out to almost 800 nm.

Another specific variation of the embodiment uses a VIB LED overlaid with a 0.1-0.2 mm thick translucent layer containing mixture of ~10-20%-620-630 nm dominant peak emission phosphor and ~10-15%-650 nm dominant peak emission phosphor, with a second 0.2 mm thick translucent layer containing a ~0.2% concentration of ~670 nm perylene dye or a 660-700 nm phosphor or QDs can produce ONIR light with almost uniform intensity over the 620-700 nm spectral range. These spectrum converters may be driven by light sources in the 390-480 nm of violet-to-blue light (VIB), phosphor-converted VIB light using phosphors with emission peaks within the 595-700 nm spectral range, or by 580-660 nm orange-to-red light (OR). Cascades of dyes may be used.

The discussion now shifts to overall assembly of the apparatus, but the spectrum converters described above provide some of the most important core technology that has not been applied to this area before. The arrangement of these LEDs and color converters is important for an optimal wearable therapeutic and/or diagnostic light source when a linear or area arrangement of the LEDs is used. The area surrounding the LEDs should be substantially light reflective in the spectral ranges to be output by the light source (not necessarily specular or mirror-like), partial thermal isolation (<0.5 W/m·K overall forward heat transfer to tissue surface) is provided between the target surface to be illuminated and the LEDs, and one or more heat removal paths must be provided. This invention describes multiple new heat removal paths are provided that may be used independently or together.

The discussion now shifts to basically how and why we assemble the LEDs and converters in a device. Specifically, the LEDs used in this light source may be arranged linearly, over an area, or at the perimeter of light guides, in addition to other arrangements. A material in a grid-and-channel device structure is placed between the tissue surface and the light devices that can (1) remove heat from the illuminated tissue surface by conduction and/or convection, (2) minimize heat transfer from the light sources to the material to the tissue surface while allowing the majority of the desired light spectrum to reach the tissue surface, (3) reflect much of the reflected light and backscattered light from the tissue back toward the tissue, and (4) remove heat from the light sources (e.g., LEDs).

Overall structure Embodiment 1: In an example embodiment of the overall structure of invention, LEDs and spectrum converter structures, such as are provided for in Embodiments 1, 2, and/or 3, are arranged on linear thermal-conducting strips or area arrays. These LED strips or arrays are mounted onto a flexible high-thermal conductivity base as a flexible heat sink using a thermal-conducting adhesive, gel, or compliant material such as soft thermal conduction silicone like is used for heat removal from integrated circuit (IC) chips. The thermally conducting and flexible backplane may include metal foil, wire grids, thermally conducting silicone with or without imbedded fabric, foil, or wire mesh. Additional heat conducting additives like ceramic, diamond particles, or carbon fibers are optional.

Small rigid high power LED modules such as 6×1 cm or 8×1 cm strips may be placed together much like a tank tread with the connecting wires for the modules. This can permit more robust heat sinking to a thermal conducting material underneath similar to using the fully flexible strips and can provide adequate flexibility for many applications, especially when forming a cylinder or partial cylinder to better bring light to some part of the body from multiple angles.

For example, light therapy on a deep knee injury can be far more effective if the light can be brought in from all 360 degrees. Low light flux deep in tissue can be augmented by light from multiple angles to provide an effective higher light dose deeper in the tissue for a given incident radiant power and treatment time.

In another preferred embodiment of this invention, violet-blue LEDs are first over 50% converted to deep red using a red-near IR phosphor (e.g., 650 nm peak phosphor), and then further shifted into the deep red and near-infra red using a thin flexible second polymer sheet (such as acrylic, PVC, polyurethane, or polycarbonate) containing an organic fluorescent dye (e.g., 600-670 nm emission peak dye or over 650 nm emission peak QDs). The phosphor and dye concentrations, and film thicknesses are adjusted to absorb almost all the violet-blue (LEDs with a dominant peak between 410 nm and 465 nm, preferably at 420 nm), but still pass 1%-15% of the blue-violet. This embodiment uniquely provides light energy in the violet range (e.g. 5% of the light energy), a dominant peak at 650 nm and 670 nm (50-50 mix) for shallow-medium biological process activation, and a long dye+phosphor emission spectrum tail past 800 nm for deeper penetrating biological process activation. If supplemented with 780-830 nm and/or 840-850 nm dominant peak LEDs, an effective spectral range of 595-880 nm can be achieved (e.g., 595-780 nm, ~800-820 nm, and ~835-850 nm or 760-790 nm, LEDs). However, one or more spectral peaks in just the 760 nm-860 nm range may be considered adequate for many applications. Shifting over 650 nm or 670 nm light to longer wavelengths may be desired and can be accomplished with appropriate color shifting materials such as by using a 700 nm-850 nm emitting dye and or one or more type 700 nm-850 QD the same way as is disclosed herein.

The disclosed color-converted light source assembly is placed onto a grid of high-translucence silicone cells and channels to reduce conductive heat transfer through this translucent grid and/or to provide peristaltic assisted and/or convection channels for heat removal. Air channels are provided for in this example. The peristaltic pumping of air action is powered by intentional or unintentional pressure or movements of the users in this example, but could also be powered by piezoelectric or other transducers mounted along the channels. Pockets, bubbles, or pillars are examples shown to further soften the surface of the light source and to further reduce heat transfer to the tissue surface, channel more light though hair, and/or to provide heat removal from the tissue surface.

This invention provides a flexible heat sink for backside heat removal in combination with a new integrated peristaltic air and convection channel based heat removal system that uses heat and/or body movements to increase air flow for heat removal from the target (e.g., tissue surface) side of the light source.

Another novel aspect of this invention is unique integration methods for heat-insulating air pockets to reduce heat transfer to the skin from the LEDs.

One embodiment of this new conformable light source utilizes a peristaltic air pump heat removal device structure powered by an integrated channel system that utilizes body movements along with convection, heat conduction, and radiation cooling. These peristaltic chambers can pump or channel air, gas, or liquids into and out of the light source to remove additional heat from the LEDs and/or cool the skin using body movements, compression, and/or other mechanical forces.

The ability to utilize these integrated passive and active heat removal processes permits higher light intensities to be used in a near tissue surface, conformal system with less heat related discomfort.

This disclosed structure can also permit air flow around the backside radiator and includes novel heat-conductive belt loops that can act as part of the heat removal-radiator system. Also, this invention discloses a novel use of a heat conductive flexible strap that can act as part of the passive heat removal system if, for example, the strap is made heat conductive using carbon fibers, metal fibers and/or heat conductive materials such as heat-conductive silicone. This strap can optimally be part of or the same as the strap(s) that would hold the light source in place on the body.

An optional opaque or partial-reflective perimeter cushion may be included to reduce physical pressure on the treated area, reduce tissue surface contact area, to provide an additional potential cooling air flow path, and to reduce light leakage laterally. Additional air flow across the tissue surface is accomplished by open sections of this cushion or by providing through-vents or pumped area though the cushion.

In one embodiment, the LEDs are mounted using a thermally conductive adhesive or by compression onto a flexible and/or segmented heat sink such as thermal silicone sheet material, carbon and/or metal fiber flexible composite materials, graphite strips, or metal foil with over 0.5 W/m·K vertical and horizontal thermal conductivity. This heat sink provides a heat transfer pathway to the ambient temperature air on the backside of the heat sink. The backside of the heat sink may be cooled by ambient air heat transfer from its surface. The backside surface of the heat sink may have an increased surface area for improving heat-to-air transfer or an attached high surface area heat exchanger.

The heat sink system may include a flexible heat conductive strap material behind and in partial or full contact with the backside heat sink material to further increase heat dissipation (e.g., a thermal conductive silicone or other heat conductor with fabric inlay or backing for strength.

Optionally, the area in front of the LEDs and/or behind the backside heat sink can be actively-cooled using a pumped liquid coolant, a peltic cooler, or forced air cooling using a blower or fan.

In another embodiment of this light source, pumped air or pumped coolant (e.g., water) through these channels is used to further reduce the tissue surface temperature and to permit higher light intensities to be used.

In another embodiment of this light source, air or liquid coolant flowing through transparent channels or bladders (through one or more channels) between the targeted surface and the light source are used to remove even more heat from the tissue surface, allowing much higher intensity light to reasonably thermal conductivity material such as transparent silicone and no thicker than necessary for structural stability. This method can remove heat directly from the tissue surface, including removal of some heat generated by the absorption of the therapeutic spectrum itself by the tissue surface. This added active cooling can be combined with the active cooling using internal air or liquid coolant channels. Alternately, fans or blowers with air channels consisting of rib-cage like heat sinks may be utilized to remove heat from the device and still permit flexibility.

According to another aspect of the present invention, there is provided a light source for therapy and/or diagnosis, comprising one or more flexible light pipes, light channels, or large area light panel (s) with perimeter mounted LEDs, or with LEDs conforming with the shape of an external area to be treated or exposed to light.

These same light channels, or additional light channels, can also be used to collect and deliver light reflected from or emitted from the target (e.g. skin or tissue) to sensors in the light source device. These sensors may be spectrometers, thermal IR sensors, or simple photocells with optical filters to assess the spectrum reflected or emitted from the target. The reflected spectrum can be used to assess the skin reflection and absorption for target surface heat and light dosimetry, or for assessing the presence and concentration of fluorescent or phosphorescent compounds such as photosensitizers, biological materials, or other materials. The light pipes or light panels may be provided with a structure on either the front or back surface as indentations, bumps, or columns to improve uniformly of light distribution or to reduce heat transfer through the material. Forced air or liquid heat removal is also anticipated from the surface of the device, perimeter, or one or more internal heat removal channels.

According to another embodiment, a method of selective photodynamic therapy comprises: introducing the selective photoluminescent compound to a body having a target cell, wherein the selective photoluminescent compound is configured to selectively attach to or enter the target cell; introducing an activating light to the selective photoluminescent compound, wherein the photoluminescent compound is configured to absorb the activating light and emit an emission light having a different wavelength than the activating light; and activating a photocytotoxic compound with the emission light of the selective photoluminescent compound.

According to yet another embodiment, a light source comprises: a light pathway including converted spectra configured to transmit a light of a first wavelength; and a tip section having a photoluminescent material located along the light pathway, the light of the first wavelength configured to be received by the photoluminescent material of the tip section and emitted from the light source as an emitted light having a second wavelength.

Photoluminescent dyes, phosphors, and quantum dots can be mixed and suspended in a variety of polymers or other translucent medium materials such as silicones, silicates, sol gels, polymers and can be painted on surfaces or shaped into structures such as lenses or in sheets.

The present invention may be incorporated into a device which is either stationary or portable and/or wearable. The light source may be incorporated into materials which are rigid such as plastics, composites, or metal housings, or into flexible materials such as silicone. This invention may also be built into a variety of fabric designs.

The discussion now shifts to additional specific embodiments of various structures and features of the present invention and its components.

The present invention provides for an array of light-emitting diodes (LEDs) as a light source for therapy and/or diagnostics or other applications, comprising an array of 2 or more light-emitting diodes with at least one of the LEDs overlaid with spectrum-converting fluorescent and/or phosphorescent containing materials, or photonic spectrum-shifting structures such that at least 30% of the light energy from the LEDs passes through the spectrum-conversion layer(s) and is absorbed by these layers. After the spectrum-converters, over 50% of the modified photon flux must contain light in 595-860 nm spectral range. LEDs without spectrum-converters in the array, if any, must contain at least one LED of either dominant peak wavelengths within the 400 nm to 495 nm spectral range, and/or dominant peak wavelengths within the 580 nm to 950 nm spectral range.

An embodiment of the present invention provides for LEDs that are arranged on a flexible heat-sinking backplane with over 0.5 W/m·K thermal conductivity, and with one or more soft translucent window layers above the LEDs. The to-be-spectrum-converted LEDs in the array have emission spectra substantially in the range 360 to 640 nm range before the spectral converters. The dominant peak emission of the to-be-spectrum-converted LED(s) is in the 400 nm to 450 nm range, the spectrum-conversion material over the to-be-converted-LEDs is a phosphor and/or fluorescent or phosphorescent dye and/or quantum dot containing layer, and/or photonic crystal lattice with the majority of the layer's light absorption spectrum in the under 460 nm range, and over 70% of the light emission of the dye or phosphor is within the 595-860 nm spectral range.

An embodiment of the present invention provides for a light source where the spectrum conversion material is a phosphor, fluorescent or phosphorescent dye, and/or quantum dots with substantial light absorption in the under 480 nm spectral range, and/or a fluorescent dye, QD, or photonic crystal structure with the majority of its absorption spectrum in the under 650 nm spectral range, and where over 70% of the light emission from the color-conversion layer(s) is within the 595 nm to 860 nm spectral range.

An embodiment of the present invention provides for a light source where up to 15% of the non-converted photon flux from the before-spectral-conversion-LEDs is in the 350 nm-465 nm spectral range for antibacterial, possible macrophage activation, possible collagen restructure initiation, blue-to-violet wavelength photosensitive chemical activation based treatments coupled with red to near-infrared spectral range based treatments.

An embodiment of the present invention provides for a light source where additional LEDs without spectrum converters may be also used to add light energy to parts of the spectrum between 350 nm and 450 nm, or between 595 nm and 950 nm.

An embodiment of the present invention provides for a phosphor layer where the phosphor(s) are in the 1%-40% concentration range within a highly-translucent matrix or sol gel, silicate, silicone, or organic polymer and exhibits an internal quantum efficiency over 60%, and/or where a fluorescent dye or quantum dot based spectrum-converter(s) is dissolved in the 0.05%-10% concentration in an organic polymer or other highly-translucent material placed between the LEDs and the target to be illuminated. (The thickness and concentrations of the spectrum converting films are adjusted to provide the desired spectral characteristics for a specific treatment.)

An embodiment of the present invention provides for a light source where the area immediately surrounding the LEDs or surrounding the LED's flexible printed circuit board strips is at least 40% reflective to, or non-absorbing of light in the 595 nm to 860 nm spectral range.

An embodiment of the present invention provides for a light source where the area in front of the LEDs is one or more translucent windows providing low thermal conduction in the direction of the under 860 nm light. A grid of air or gas pockets and/or air channels is claimed with at least one solid zone of highly translucent material placed between the target to be illuminated and the LEDs.

An embodiment of the present invention provides for a backside's heatsink structure that permits air flow around the backside radiator and includes belt loops that act as part of the heat removal system, minimizing the effect of elastic straps.

An embodiment of the present invention provides for a light source where the area in front of the LEDs is one or more translucent windows providing low thermal conduction in the direction of the under 960 nm light. A grid of liquid, air, or gas pockets with channels that can allow peristaltic air pumping when the LED light source is bent and/or moved to increase convection flow to assist in the removal of heat from the front side of the LED array.

An embodiment of the present invention provides for a light source according to claim 13, where the channels contain pumped air or liquid coolant.

An embodiment of the present invention provides for a light source where the area in front of the LEDs is one or more translucent windows providing low thermal conduction in the direction of the under 960 nm light. In such embodiment, grid vertical wall structures (e.g., bowl, box, or honeycomb-like) facing the target-to-be-illuminated surface provides reduced conductive heat transmission because of additional air gaps and/or provide a small reservoir for skin or tissue surface lotions, gels, or liquids.

An embodiment of the present invention provides for a light source where the area in front of the LEDs is one or more highly translucent windows providing active heat removal. Air or liquid coolant channels are claimed with at least one solid sheet of highly translucent material between the target to be illuminated and the LEDs.

An embodiment of the present invention provides for a light source where a flexible layer is placed in front of the LEDs that is one or more translucent windows that is also partly-reflective or partly-blocking to infrared (IR) light, such as IR absorbing films, dichroic filters, or using other types of interference filters or photonic lattice arrays.

An embodiment of the present invention provides for a light source where the area surrounding most of the perimeter of translucent window(s) over the LEDs is a raised mostly-opaque structure to act as a soft cushion if placed against the tissue surface and to reduce lateral light. The cushion structure or material may be a soft-solid, tubular, bladder, or partly coiled structure. The cushion structure can be reflective, partly-reflective, or mostly opaque to light primarily in the 400-460 nm and 595-860 nm spectral range.

An embodiment of the present invention provides for a light source where one or more light sensors are placed in or near the LED array, facing toward the target of the illumination, that detect reflected light from the target. These sensor(s) are to be provided with a circuit to adjust the light intensity based on tissue surface reflectivity at the wavelength ranges being used. Multiple sensors sensitive to different wavelength ranges are claimed for the detection of preferential reflected wavelengths of light and to permit manual or automatic adjustment of relative power to the mixture of different color LEDs.

An embodiment of the present invention provides for a light source where one or more Infrared light sensors are placed in or near the LED array, facing toward the target of the illumination that detect heat at the target. These sensor(s) are to be provided with a circuit to adjust the light intensity based on tissue surface temperature.

An embodiment of the present invention provides for a light source where the infrared sensor self-calibrates to the tissue surface temperature prior to activation of the LED light sources, allowing control based on a change in tissue surface temperature and/or actual tissue surface temperature. This system would provide an automatic feedback warning or shut off at predetermined levels.

An embodiment of the present invention provides for a light source where the temperature or other sensors are placed on or in the patient's tissue to measure surface temperature before, during, and/or after the treatment. Temperature monitoring may be in the light treatment zone or elsewhere. Feedback from these sensors are for allowing control based on a change in tissue surface temperature and/or actual tissue surface temperature, or other parameters based on the type of sensor and data gathered. This system could provide an automatic feedback warning or shut off at predetermined levels.

An embodiment of the present invention provides for a light source where the controller can call an attendant to a patient a designated amount of time before the treatment time has ended or when the treatment has completed, when the patient turns off the system or presses a call button, a system failure occurs, and any of several other conditions or situations.

An embodiment of the present invention provides for a light source where one or more temperature sensors are placed in the LED array and/or near surface of the, facing toward the target of the illumination, that can be used to control temperature by adjusting the LED intensity, or for providing a warning or automatic shut off power if the temperature of the array or transparent pad surface exceeds an approximate predetermined value.

An embodiment of the present invention provides for a light source where vibrating (6-2000 Hz) and/or ultrasonic transducers (Over 20,000 Hz and under 110 MHz) are placed in the proximity of the LED array to enhance the effectiveness of the light sources alone, or when used with liquid or cream tissue surface treatments, cosmetics, or photosensitizers by opening pores, increasing the transport of compounds through cell membranes, and potentially increasing blood or lymph fluid flow.

An embodiment of the present invention provides for a light source where the translucent light emitting portion of the source is a pad between at least 1 cm wide by 1 cm long, and up to 0.5 meters in length and up to 0.3 meters wide that can placed around the afflicted area of the body, or placed over, under, or beside the target to be illuminated.

An embodiment of the present invention provides for a light source where the light source is a long light emitting pad between 0.5 meters long and 50 meters long of any practical width that can be coiled around the afflicted area(s) of the body, or otherwise placed around, over, under, or beside the target to be illuminated.

An embodiment of the present invention provides for a light source where the light source is a partial or full body system with the light source providing light therapy from 2 or more sides simultaneously. An embodiment of the present invention provides for a light source where the light source is a light emitting pad used for wound healing and other tissue surface, tissue, or inflammation treatments with a very soft jelly like silicone or similar transparent surface against the tissue surface. A perimeter ridge can be placed to further hold in any creams of liquids against the tissue surface.

An embodiment of the present invention provides for a light source where surface of the soft material, as described above, is indented with dimples or formed into bumps, formed into an egg-crate grid, or formed into a large number of finger-like or other cross-section shaped protrusions to further soften the surface and hold photosensitizers, emoluments, antimicrobial or antibiotic materials, and/or other creams, gels, or liquids for long term contact with the tissue surface. A perimeter ridge is optionally placed to further hold in any creams, gels, or liquids against the tissue surface.

An embodiment of the present invention provides for the surface of the soft material against the tissue surface, as described above, to consist of an array of translucent columns, bumps, or other extensions to improve light transmission through hair and reduce tissue surface heating.

An embodiment of the present invention provides for a strap mechanism to hold the treatment system in place on the patient. The strap can be a belt going through belt loops on the light therapy system with any number of fastening methods. Said belt may be made thermally conducting to further assist in heat removal from the back the system.

An embodiment of the present invention provides for a strap mechanism to hold the treatment system in place on the patient. The strap can be connected to the device by Velcro, buttons, snaps, zippers, clamps, adhesives, gels, suction, or any other adequate system that can hold the light therapy system in place.

An embodiment of the present invention provides for a mechanism to hold area light therapy system modules on or near the patient. The mechanism may be a mechanical system holding 2 or more LED arrays in specific positions and distance from the patient treatment system in place on the patient or a system that can be shaped to large portions of the patient body. The mechanisms holding the light therapy system may be frames, adjustable brackets, or of the building tanning bed or booth like, mobile or primarily stationary.

Patients may use disposable or reusable transparent materials over their skin to minimize contamination of the light therapy system or the patient. Examples would be clear plastic or silicone arm or leg covers, or other type of partial or full body covers.

An embodiment of the present invention provides for a light source that positions the LED toward bundles of multiple fiber optic loops or coils to concentrate the light in a forward direction or other designed direction.

An embodiment of the present invention provides for a light source that positions the LEDs toward bundles of fiber optic loops or coils to concentrate the light in a forward direction and uses phosphor, quantum dot, fluorescent or phosphorescent dye doped fibers, and/or photonic crystal fibers to provide all or part of the LED's spectrum conversion, including the optional creation of coherent fiber laser light sources.

An embodiment of the present invention provides for a method using a light source that places a large area light source (area over 50 cm2) in area on the head, and/or neck, using straps or head gear for increasing the generation of nerve stem cells in the brain, or spine, traumatic brain injury treatments, pain reduction, and for mood treatments.

An embodiment of the present invention provides for a method using a light source that places a large area light source (area over 50 cm2) on the body for improving internal organ function or accelerating tissue repair.

An embodiment of the present invention provides for a method using a light source, that places a light source over wounds for improving healing and tissue surfaces, dermatology treatments, pain reduction, and/or tissue regeneration.

An embodiment of the present invention provides for a method using a light source that places a large area light source (area over 50 cm2) on the body for enhancing muscle growth during or after exercise.

An embodiment of the present invention provides for a method using a light source that places a large area light source (area over 50 $cm^2$) on the body such as joints and muscles for improving tissue regeneration, pain reduction, and inflammation reduction.

An embodiment of the present invention provides for a method using a light source that places a large area light source (area over 50 $cm^2$) for veterinary use for tissue regeneration, pain reduction, and inflammation reduction.

An embodiment of the present invention provides for a light source where the light source is used to provide energy for botanical plant or algae growth.

An embodiment of the present invention provides for a light source where the light source is used for purification and antimicrobial treating of water or body fluids, with or without an added photosensitizer.

An embodiment of the present invention provides for a light source where the light spectrum converter without the heat sink or translucent heat barrier opposite the light source that is used for enhanced botanical plant or algae growth, or for purification and antimicrobial treating of water or body fluids, with or without an added photosensitizer.

An embodiment of the present invention provides for a light source including 2 or more over 5 gauss magnets, with said magnets preferentially arranged in an alternating North-South patterns, and mechanically moved or reversed as required. Electromagnets may also be optionally not used, used continuously, pulsed, or reversed.

An embodiment of the present invention provides for a light including with 1 or more piezoelectric, capacitive, inductive, or magnetostrictive transducers, or motors to generate ultrasonic energy and/or vibration from the light source in continuous and/or pulsed energy.

An embodiment of the present invention provides for a light source including electrodes to provide pulsed AC current to stimulate tissue surface and tissue locally under and/or near the light source.

An embodiment of the present invention provides for a combination of all or any subset of the integrated technologies provided above.

An embodiment of the present invention provides for utilization of the light source(s), and/or certain components thereof described herein, for various applications not specifically listed herein, including but not limited to the fields of medicine, veterinary, biomass growth and control, horticulture, cosmetics, photodynamic therapy (PDT), low level light therapy (LLLT), light influenced biological processes, diagnostics, lighting for photo-luminescent based imaging, and/or other medical or non-medical applications.

The present invention, or embodiments thereof which may use all or parts of the described spectral ranges, is applicable to light therapy devices and methodologies including but not limited to (1) Low level light therapy (LLLT) for the treatment of inflammation and/or for tissue surface, other tissue healing, skin and tissue rejuvenation, muscle growth enhancement, muscle repair and pain reduction, accelerated tendon healing, joint or cartilage treatments, plantar fasciitis, pain management, traumatic brain injury (TBI) damage risk reduction, neurologic rejuvenation, enhancing stem cell generation, enhancing mood, and/or enhanced rate healing of wounds, blood and body fluid treatments (with or without photosensitizers), spider vein and/or varicose vein and/or scar and/or stretch mark reduction treatments with or without photosensitizers, reducing arterial plaques or other undesired biological materials using photosensitizers, treating biofilms on natural and/or man-made surfaces in or on the body, carpal tunnel, fibromyalgia, tendonitis, bursitis, tendonitis, migraines, carpel tunnel, osteoarthritis, dental root and implant healing or bone regrowth, for enhancing the rate for other bone healing, accelerating T-cell life cycles and activity, accelerating macrophage action, veterinary applications, and/or providing many other health related medical benefits, (2) activation of photosensitizers used in Photodynamic therapy (PDT) for cancer or antimicrobial treatments using natural or synthetic photosensitizers, including photosensitizers produced by bacteria in or on the body, (3) imaging and diagnostics using the emitted light spectral range, (4) Intense Pulsed Light (IPL) therapies, sidereal or other mood therapies, (5) activation of adhesives or scaffolding agents as a part of reconstructive or cosmetic surgery, (6) photoactivation of release agents to separate structures of compounds for surfaces, (7) powering of photocell driven devices in the body, and/or (8) other uses such as light-sensitive chemical activation, and/or use of this light therapy in combination with ultrasonic, vibration, thermal heating or cooling, and other combinational therapies.

cooling system for a flexible LED array consisting of: Multiple LEDs mounted on a flexible PCB with openings or heat-conductive material under and/or around each LED to provide a pathway for heat to underlying heat sinks using, braising, solders, or eutectic bonding, conductive composite materials, low melting point metal alloys, thermally conductive grease, and/or thermally conductive adhesive materials.

A heatsink consisting of a thermally conducting material such as graphite, metal such as aluminum, plated or laminated metals, thermally conductive composites such as thermal conductive silicone or flexible carbon fiber, diamond particles, or metal fiber composites. These structures can be arrays of multiple rigid plates to effectively create a flexible tiled structure that are held together or may be flexible structures. Multiple layers of these materials may be used.

A cooling system consisting of a flexible molded or assembly of sheet material such as silicone or other polymers on the backside opposite the LEDs. This structure will have one of more electrical conductors in or on the polymer structured to perform as a bellows. The electrical conductor sheets to be covered or be coated with an insulating material to be minimally vertically conductive, and/or the opposing heat sink surface should be covered or coated to be minimally electrically conductive vertically. The heat sink or conductor placed over the heat sink may be used as a second electrode.

Standoffs between each pair of electrical conductors so that they remain apart unless forced together. These standoffs can be formed when molding one of either side of the bellows or added to the structure to the gap as separate components.

Placing an electrical change between these plates creates an electric force that can pull the plates together and push air out, and when release they can pull air in.

The bellows may be one or more large or long sections that can push most of the air out from between the conductors, can be a series of bellows that sequentially are activated by a controller to push air linearly in any selected direction, and/or can be configured as one or more smaller bellows that push part of the air in one direction due to check values built into the air part so air travels primarily in one direction for each channel.

If check value are used, they can be prefabricated and inserted into the channels during assembly, or the check values can be made as part of the structure when one or both sides of the channel are moulded. The check vales may be simple flaps with a preferred direct and be blocked from reversing direction with molded in ridges.

High dielectric constant materials such as epoxy/barium titanate coating composites are preferred over these conductor plates to reduce the required drive voltage.

Magnets, conductive coils, and/or ferromagnetic materials may be substituted for the electric to provide motive force to these bellows. While bellows pumping mechanisms are known using similar components to those presented. What makes this structure unique is the significant and unusual adaptations for use a flexible array, the built in molded check valves, and being used as a built in dual purpose heat sink and cooling airflow generator for large area flexible devices. This cooling mechanism makes it possible to manufacture low cost, thin, reliable devices than can remain cooler and/or handle much higher power than reasonable thickness systems with passive heat removal systems.

A drawing showing an embodiment of this concept with novel molded in check valves.

The present invention, or embodiments thereof which may use all or parts of the described spectral ranges, is applicable to non-therapy biological uses of devices including but not limited to (1) enhancing plant growth, blooming, and/or ripening, (2) enhancing algae growth, photo-bacteria growth, and other photosynthesis or other photosensitive biological processes, (3) microbial stimulation, (4) increasing antimicrobial action on or in materials using photosensitizers (e.g., water or foods), and/or (5) visual image enhancement for enhanced detection of materials with unique light absorption and emission characteristics.

While the foregoing written description of the invention enables one of ordinary skill to make and use what is considered presently to be the best mode or modes thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. The disclosure, as variously set out herein in respect of features, aspects and embodiments thereof, may in particular implementations be constituted as comprising, consisting, or consisting essentially of, some or all of such features, aspects and embodiments, as well as elements and components thereof, or a selected one or ones thereof, being aggregated to constitute various further implementations of the disclosure. The disclosure contemplates such features, aspects and embodiments in various permutations and combinations, as being within the scope of the disclosure. The disclosed subject matter may therefore be specified as comprising, consisting or consisting essentially of, any of such combinations and permutations of these specific features, aspects and embodiments, or a selected one or ones thereof.

What is claimed is:

1. A light emitting device for generating a predominantly non-coherent output light, comprising one or more spectrum converters, one or more LEDs, and one or more power supplies arranged for energizing the one or more LEDs, wherein the device is configured to produce the output light with an output photon flux that is predominantly in the orange-to-near-infrared (ONIR) 595 nm-960 nm spectral range, and with light energy at all wavelengths within such ONIR spectral range, wherein the light emitting device exhibits all the following characteristics:
   (a) one or more of the LEDs are overlaid with one or more spectrum-converting fluorescent and/or phosphorescent containing materials or photonic spectrum-shifting structures, as said spectrum converters;
   (b) the LEDs and spectrum converters in the light emitting device are configured so that LED light converted by the spectrum converters contributes over 25% of the total output radiant light power of the output light;
   (c) internal quantum yield of spectrum converters averages over 60% when independent of the light emitting device and under optimal conditions;
   (d) one(s) of the one or more LEDs to be spectrum converted provide dominant spectral emission peaks between 350 nm and 480 nm and/or between 590 and 780 nm;
   (e) 350 nm and 480 nm dominant peak LEDs with spectrum converters use a phosphor or QD as the spectrum converter for absorption of over 70% of the normal angle LED radiant power light;
   (f) 600 nm-780 nm dominant emission peak LEDs with spectrum converters use a fluorescent dye or QD spectrum converter for absorption of over 30% of the normal angle LED radiant power light;
   (g) over 70% of the total output light from the device is in the 595-960 nm spectral range;
   (h) at least 1% of the highest radiant power peak in the 600 nm-750 nm part of the emitted light spectrum of the output light is provided at all wavelengths between 600 nm and 820 nm;
   (i) LED(s) of the one or more LEDs, whose light is not significantly absorbed by the spectrum converters comprise LEDs with dominant peak wavelengths within the 350 nm-480 nm spectral range and/or within the 650 nm to 960 nm spectral range;
   (j) the device comprises a lighted window at which the light output is emitted, and the device provides at least 5 mW/cm$^2$ average radiant power output in a primary lighted portion of the lighted window and the primary lighted portion of the lighted window comprises a lighted area of at least 4 cm$^2$;
   (k) at least 60% of the area of the primary lighted portion of the lighted window contains over 30% reflective surfaces at the highest spectral emission peak of the output light, not including area used by LEDs or spectrum converters, to reflect light back into the output light;
   (l) LED light is provided by at least one of the one or more LEDs behind the lighted window, in the perimeter of the lighted window, or brought to the lighted window using fiber optics;
   (m) a thermal controller is arranged to interrupt or reduce power from the one or more power supplies when the temperature at the LED heat sink or at the LEDs inside the device exceeds a predetermined value; and
   (n) wherein when the LED light is not brought to the window by fiber optics, the thermal controller is effective to prevent the light-output side surface temperature of the device from exceeding 70° C. after 60 minutes of device operation in a 35° C. ambient environment.

2. The device of claim 1, wherein the spectrum converters comprise a phosphor, fluorescent or phosphorescent dye, and/or quantum dots with substantial light absorption in the under 480 nm spectral range, and/or a fluorescent dye or photonic crystal structure with the majority of its absorption spectrum in the under 650 nm spectral range, and where over 70% of light emission from the spectral converters is within the 595 nm to 950 nm spectral range.

3. The device of claim 1, comprising rows or columns of said LEDs on one or more flexible circuit connection backing arrangements, and/or comprising a multiplicity of rigid LED modules that can be placed so as to provide therapy light from two or more angles.

4. The device of claim 1, comprising control circuitry configured to operate the device at a constant luminance, or modulated at one or more frequencies and at one or more duty cycles.

5. The device of claim 1, comprising a backside heat sink structure comprising heat conducting belt loops configured to dissipate at least 25% of the total heat load from the one or more LEDs and/or comprising sections of heat conducting belts in contact with said belt loops.

6. The device of claim 1, comprising a backside heat sink structure that permits air flow around and/or through a backside radiator that includes four or more heat conducting materials formed as fins, waves, tubes, or folds bonded to a heat conducting base structure.

7. The device of claim 1, comprising a backside heat sink structure.

8. The device of claim 1, wherein the lighted window comprises one or more windows on a top side of the device where the light output is emitted, wherein
- the active-light window area in front of the LEDs has one or more translucent windows providing low thermal conduction to the skin or other tissue, comprising a 2D or 3D matrix of liquid, gel, or air filled gas pockets or channels, and comprising low-thermal conducting top surface materials;
- air or gas is flowed through the pockets or channels to improve heat removal;
- bumps and/or raised patterns and/or recessed patterns are disposed between two or more transparent layers between the one or more LEDs and the windows;
- bumps or fiber-like extensions of surface material, or a matrix of LED-coupled fibers protrudes through a window;
- a top outer surface of a window comprises a grid of wells to provide air pockets to reduce heat transfer through the windows and/or to hold materials for application to the skin; and/or
- the lighted window is formed of a low index of refraction silicone or multiple layers of low index of refraction coatings or films are provided at a surface of the lighted window.

9. The device of claim 1, comprising a monitoring and control assembly including one or more light sensors placed in, on, and/or near the lighted window, facing toward a target surface when the device is in use so that the sensor(s) detect reflected light from the target, with the sensor(s) arranged to provide input to a controller circuit to adjust light intensity based on reflectivity, and/or to adjust the time of treatment.

10. The device of claim 1, comprising a monitoring and control assembly including one or more temperature sensor(s) arranged to directly or indirectly monitor a target surface temperature and provide corresponding input to a controller configured to modify light intensity and/or treatment time of the device.

11. The device of claim 1, wherein the LEDs are positioned toward bundles of fiber optic loops or coils to concentrate light in a forward direction and comprising phosphors, quantum dots, fluorescent or phosphorescent dye, dye-doped fibers, and/or photonic crystal fibers to provide spectrum conversion.

12. The device of claim 1, comprising one or more piezoelectric, capacitive, inductive, or magnetostrictive transducers or motors to generate sonic and/or ultrasonic energy and/or vibration from, and/or in the vicinity of the output light as continuous and/or pulsed energy.

13. The device of claim 1, comprising electrodes configured to generate pulsed AC current to stimulate tissue surface and tissue locally under and near the output light.

14. The device of claim 1, comprising two or more over 5 gauss magnets.

15. The device of claim 1, comprising one or more controllers that are programmed to turn the device off at an end of a programmed time.

16. The device of claim 1, comprising at least one of: (i) a cooling system configured to pump or suction air through an interior region of the device (ii) a cooling system configured to pump or suction air over a heat sink in the device, and (iii) a water recirculation heat exchanger.

17. The device of claim 1, comprising a diaphragm or bellows air pumped cooling system.

18. The device of claim 1, wherein the one or more LEDs comprise an LED array, and wherein the device comprises channels arranged for peristaltic air pumping when the device is bent and/or moved, to increase convection flow in and out of the channels to effect heat removal from the LED array.

19. A method of light therapy treatment of a subject in need thereof, said method comprising generating a modified light spectrum output, and exposing a body region of the subject to the light output thereof, wherein the modified light spectrum output is a predominantly non-coherent output light that is generated by a light emitting device comprising one or more spectrum converters, one or more LEDs, and one or more power supplies arranged for energizing the one or more LEDs, wherein the device is configured to produce the output light with an output photon flux that is predominantly in the orange-to-near-infrared (ONIR) 595 nm-960 nm spectral range, and with light energy at all wavelengths within such ONIR spectral range, wherein the light emitting device exhibits all the following characteristics:
- (a) one or more of the LEDs are overlaid with one or more spectrum-converting fluorescent and/or phosphorescent containing materials or photonic spectrum-shifting structures, as said spectrum converters;
- (b) the LEDs and spectrum converters in the light emitting device are configured so that LED light converted by the spectrum converters contributes over 25% of the total output radiant light power of the output light;
- (c) internal Quantum yield of spectrum converters averages over 60% when independent of the light emitting device and under optimal conditions;
- (d) one(s) of the one or more LEDs to be spectrum converted provide dominant spectral emission peaks between 350 nm and 480 nm and/or between 590 and 780 nm;
- (e) 350 nm and 480 nm dominant peak LEDs with spectrum converters use a phosphor or QD as the spectrum converter for absorption of over 70% of the normal angle LED radiant Dower light;
- (f) 600 nm-780 nm dominant emission peak LEDs with spectrum converters use a fluorescent dye or QD spectrum converter for absorption of over 30% of the normal angle LED radiant power light;
- (g) over 70% of the total output light from the device is in the 595-960 nm spectral range;
- (h) at least 1% of the highest radiant power peak in the 600 nm-750 nm part of the emitted light spectrum of the output light is provided at all wavelengths between 600 nm and 820 nm;
- (i) LED(s) of the one or more LEDs, whose light is not significantly absorbed by the spectrum converters comprise LEDs with dominant peak wavelengths within the 350 nm-480 nm spectral range and/or within the 650 nm to 960 nm spectral range;
- (j) the device comprises a lighted window at which the light output is emitted, and the device provides at least 5 mW/cm$^2$ average radiant power output in a primary lighted portion of the lighted window and the primary lighted portion of the lighted window comprises a lighted area of at least 4 cm$^2$;
- (k) at least 60% of the area of the primary lighted portion of the lighted window contains over 30% reflective surfaces at the highest spectral emission peak of the output light, not including area used by LEDs or spectrum converters, to reflect light back into the output light;

(l) LED light is provided by at least one of the one or more LEDs behind the lighted window, in the perimeter of the lighted window, or brought to the lighted window using fiber optics;

(m) a thermal controller is arranged to interrupt or reduce power from the one or more power supplies when the temperature at the LED heat sink or at the LEDs inside the device exceeds a predetermined value; and (n) wherein when the LED light is not brought to the window by fiber optics, the thermal controller is effective to prevent the light-output side surface temperature of the device from exceeding 70° C. after 60 minutes of device operation in a 35° C. ambient environment.

20. The method of claim 19, wherein the light therapy treatment is carried out to treat:

joints and muscles for reducing pain and inflammation;

wounds for improving the rate of wound healing;

acne, rosacea, skin tone, and other dermatological conditions, to improve healing, and reduce the population of bacteria or fungus that are directly or indirectly photosensitive to the light spectrum of the light therapy treatment;

muscles for enhancing regeneration of tissue after exercise or other stress;

bone areas to repair damage and improve bone density;

head, neck, spine, or other body areas, for pain and inflammation, for mood treatments, for reducing damage from brain injuries, or for increasing generation of nerve stem cell;

veterinary subjects;

photochemicals from food, herbs, and/or photochemical drugs for phototherapies;

plants to enhance plant or algae growth or to control other plant functions selected from the group consisting of ripening, seed formation, and bud formation; or water and other fluids to activate photosensitizers for purification and/or antimicrobial and/or other pathogen treatments.

* * * * *

UNITED STATES PATENT AND TRADEMARK OFFICE
CERTIFICATE OF CORRECTION

| | | |
|---|---|---|
| PATENT NO. | : 8,858,607 B1 | Page 1 of 1 |
| APPLICATION NO. | : 14/217356 | |
| DATED | : October 14, 2014 | |
| INVENTOR(S) | : Gary W. Jones | |

It is certified that error appears in the above-identified patent and that said Letters Patent is hereby corrected as shown below:

In the Specification,

Column 10, line 52: "hack" should be -- back --.

Column 14, line 26: "nm n and" should be -- nm, and --.

Column 15, line 42: "hoard" should be -- board --.

In the Claims,

Column 42, line 31: "Quantum" should be -- quantum --.

Column 42, line 41: "Dower" should be -- power --.

Signed and Sealed this
Twenty-third Day of December, 2014

Michelle K. Lee
*Deputy Director of the United States Patent and Trademark Office*